(12) United States Patent
Bruchman et al.

(10) Patent No.: US 9,737,398 B2
(45) Date of Patent: Aug. 22, 2017

(54) PROSTHETIC VALVES, FRAMES AND LEAFLETS AND METHODS THEREOF

(71) Applicant: W. L. Gore & Associates, Inc., Newark, DE (US)

(72) Inventors: William C. Bruchman, Camp Verde, AZ (US); Daniel A. Crawford, Flagstaff, AZ (US); Logan R. Hagaman, Flagstaff, AZ (US); Cody L. Hartman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 14/133,563

(22) Filed: Dec. 18, 2013

(65) Prior Publication Data

US 2014/0180400 A1    Jun. 26, 2014

Related U.S. Application Data

(60) Provisional application No. 61/802,116, filed on Mar. 15, 2013, provisional application No. 61/739,721, filed on Dec. 19, 2012.

(51) Int. Cl.
*A61F 2/24* (2006.01)

(52) U.S. Cl.
CPC .......... *A61F 2/2412* (2013.01); *A61F 2/2415* (2013.01)

(58) Field of Classification Search
None
See application file for complete search history.

(56) References Cited

U.S. PATENT DOCUMENTS

| 3,953,566 A | 4/1976 | Gore |
| 4,265,694 A | 5/1981 | Boretos et al. |
| 5,628,791 A | 5/1997 | Bokros et al. |
| 5,708,044 A | 1/1998 | Branca |
| 6,174,331 B1 | 1/2001 | Moe et al. |

(Continued)

FOREIGN PATENT DOCUMENTS

| CN | 102764169 | 11/2012 |
| FR | 2 591 100 | 6/1987 |

(Continued)

OTHER PUBLICATIONS

International Search Report for PCT/US2013/075380 mailed Mar. 3, 2014, corresponding to U.S. Appl. No. 13/869,524, 5 pages. (previously submitted on Aug. 7, 2014).

(Continued)

*Primary Examiner* — Thomas J Sweet
*Assistant Examiner* — Wade P Schutte

(57) ABSTRACT

Described embodiments are directed toward prosthetic heart valve leaflets of particular shapes that control bending character. In accordance with an embodiment, a prosthetic heart valve comprises a leaflet frame having a generally tubular shape with attached film. The leaflet frame defines a plurality of leaflet windows. The film defines at least one leaflet extending from each of the leaflet windows. Each leaflet attachment zone on the leaflet frame has substantially the shape of an isosceles trapezoid having two leaflet sides, a leaflet base and a leaflet free edge opposite the leaflet base. The two leaflet sides diverge from the leaflet base, wherein the leaflet base is substantially flat.

7 Claims, 25 Drawing Sheets

(56) References Cited

U.S. PATENT DOCUMENTS

| | | |
|---|---|---|
| 6,283,994 B1 | 9/2001 | Moe et al. |
| 6,283,995 B1 | 9/2001 | Moe et al. |
| 6,328,763 B1 | 12/2001 | Love et al. |
| 6,454,798 B1 | 9/2002 | Moe |
| 6,482,228 B1 | 11/2002 | Norred |
| 6,541,589 B1 | 4/2003 | Baillie |
| 6,562,069 B2 | 5/2003 | Cai et al. |
| 6,613,086 B1 | 9/2003 | Moe et al. |
| 6,666,885 B2 | 12/2003 | Moe |
| 6,916,338 B2 | 7/2005 | Speziali |
| 7,306,729 B2 | 12/2007 | Bacino et al. |
| 7,381,218 B2 | 6/2008 | Schreck |
| 7,462,675 B2 | 12/2008 | Chang et al. |
| 7,510,575 B2 * | 3/2009 | Spenser et al. ............ 623/2.18 |
| 7,531,611 B2 | 5/2009 | Sabol et al. |
| 7,708,775 B2 | 5/2010 | Rowe et al. |
| 7,780,725 B2 | 8/2010 | Haug et al. |
| 7,967,853 B2 | 6/2011 | Eidenschink et al. |
| 7,993,394 B2 | 8/2011 | Hariton et al. |
| 8,637,144 B2 | 1/2014 | Ford |
| 8,728,154 B2 | 5/2014 | Alkhatib |
| 8,870,948 B1 | 10/2014 | Erzberger et al. |
| 8,961,599 B2 | 2/2015 | Bruchman et al. |
| 9,139,669 B2 | 9/2015 | Xu et al. |
| 2002/0082687 A1 | 6/2002 | Moe |
| 2003/0114913 A1 | 6/2003 | Spenser |
| 2004/0024448 A1 | 2/2004 | Chang et al. |
| 2004/0243222 A1 | 12/2004 | Osborne et al. |
| 2005/0027348 A1 | 2/2005 | Case et al. |
| 2005/0137682 A1 | 6/2005 | Justino |
| 2006/0122693 A1 | 6/2006 | Biadillah et al. |
| 2006/0290027 A1 | 12/2006 | O'Connor et al. |
| 2007/0010876 A1 | 1/2007 | Salahieh et al. |
| 2007/0021826 A1 | 1/2007 | Case et al. |
| 2007/0207186 A1 | 9/2007 | Scanlon et al. |
| 2008/0009940 A1 | 1/2008 | Cribier |
| 2008/0065198 A1 | 3/2008 | Quintessenza |
| 2008/0133004 A1 | 6/2008 | White |
| 2008/0195199 A1 * | 8/2008 | Kheradvar ............ A61F 2/2418 623/2.11 |
| 2008/0220041 A1 | 9/2008 | Brito et al. |
| 2010/0036021 A1 | 2/2010 | Lee et al. |
| 2010/0082094 A1 | 4/2010 | Quadri et al. |
| 2010/0137998 A1 | 6/2010 | Sobrino-Serrano et al. |
| 2010/0185274 A1 | 7/2010 | Moaddeb et al. |
| 2010/0191320 A1 | 7/2010 | Straubinger et al. |
| 2010/0217382 A1 | 8/2010 | Chau et al. |
| 2010/0262231 A1 | 10/2010 | Tuval et al. |
| 2011/0208283 A1 | 8/2011 | Rust |
| 2011/0218619 A1 | 9/2011 | Benichou et al. |
| 2011/0251678 A1 | 10/2011 | Eidenschink et al. |
| 2012/0101567 A1 | 4/2012 | Jansen |
| 2012/0101571 A1 | 4/2012 | Thambar et al. |
| 2012/0130471 A1 | 5/2012 | Shoemaker et al. |
| 2012/0185038 A1 * | 7/2012 | Fish ............ A61F 2/2415 623/2.13 |
| 2012/0323315 A1 | 12/2012 | Bruchman et al. |
| 2014/0031924 A1 | 1/2014 | Bruchman et al. |
| 2014/0031927 A1 | 1/2014 | Bruchman et al. |
| 2014/0180400 A1 | 6/2014 | Bruchman et al. |
| 2014/0236289 A1 | 8/2014 | Alkhatib |
| 2014/0324164 A1 | 10/2014 | Gross et al. |
| 2015/0142100 A1 | 5/2015 | Morriss et al. |

FOREIGN PATENT DOCUMENTS

| | | |
|---|---|---|
| GB | 2 312 485 | 10/1997 |
| WO | 00/62716 | 10/2000 |
| WO | 2008/097592 | 8/2008 |
| WO | 2010/057262 | 5/2010 |
| WO | 2011/109450 | 9/2011 |
| WO | 2011/109801 | 9/2011 |
| WO | 2012/082952 | 6/2012 |
| WO | 2012/110767 | 8/2012 |
| WO | 2012/167131 | 12/2012 |
| WO | 2014/018432 | 1/2014 |

OTHER PUBLICATIONS

International Search Report for PCT/US2013/076504 mailed Apr. 28, 2014, corresponding to U.S. Appl. No. 14/133,491, 7 pages. (previously submitted on Aug. 7, 2014).

International Search Report for PCT/US2013/071632 mailed Apr. 28, 2014, corresponding to U.S. Appl. No. 13/841,334, 6 pages. (previously submitted on Aug. 7, 2014).

International Search Report for PCT/US2013/075380 mailed Mar. 6, 2014, corresponding to U.S. Appl. No. 13/869,524, 5 pages. (previously submitted on Aug. 7, 2014).

International Search Report for PCT/US2013/076688 mailed Feb. 27, 2014, corresponding to U.S. Appl. No. 14/133,563, 5 pages.

International Search Report for PCT/U52013/074962 mailed Feb. 27, 2014, corresponding to U.S. Appl. No. 13/833,650, 4 pages.

International Search Report for PCT/US2013/068390 mailed Apr. 29, 2014, corresponding to U.S. Appl. No. 13/835,988, 7 pages.

International Search Report for PCT/US2013/076504 mailed Feb. 27, 2014, corresponding to U.S. Appl. No. 14/133,491, 7 pages.

International Search Report for PCT/US2013/071632 mailed Mar. 18, 2014, corresponding to U.S. Appl. No. 13/841,334, 6 pages.

International Search Report for PCT/U52013/075274 mailed Feb. 27, 2014, corresponding to U.S. Appl. No. 13/843,196, 5 pages.

International Search Report for PCT/US2013/075380 mailed , corresponding to U.S. Appl. No. 13/869,524, 5 pages.

International Search Report for PCT/U52013/068780 mailed Feb. 27, 2014, corresponding to U.S. Appl. No. 13/869,878, 4 pages.

International Search Report for PCT/US2013/046389 mailed Jan. 21, 2014, corresponding to U.S. Appl. No. 13/797,633; 7 pages.

International Search Report for PCT/US2013/051431 mailed Jan. 20, 2014, corresponding to U.S. Appl. No. 13/797,526; 6 pages.

Clough, Norman E. Introducing a New Family of GORE™ ePTFE Fibers (2007).

* cited by examiner

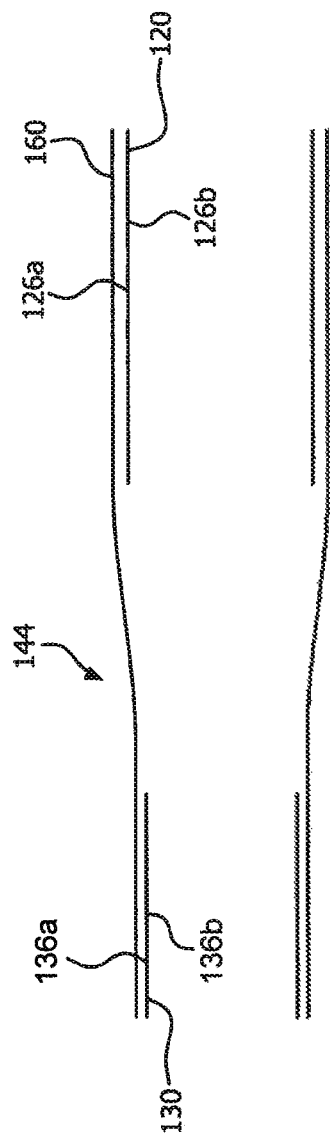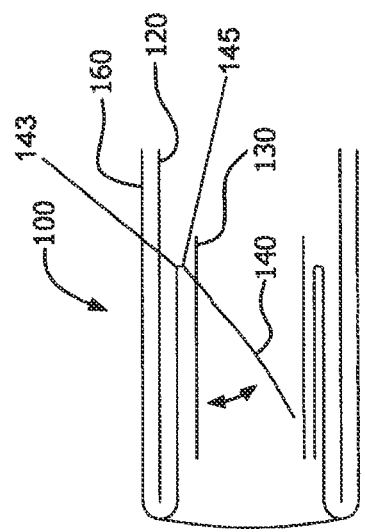

PROSTHETIC VALVES, FRAMES AND LEAFLETS AND METHODS THEREOF

FIELD

The present disclosure relates generally to prosthetic heart valves and more specifically synthetic flexible leaflet-type prosthetic heart valve devices, systems, and methods.

BACKGROUND

Bioprosthetic heart valves have been developed that attempt to mimic the function and performance of a native valve. Flexible leaflets are fabricated from biological tissue such as bovine pericardium. In some bioprosthetic heart valve designs, the biological tissue is sewn onto a relatively rigid frame that supports the leaflets and provides dimensional stability when implanted. Although bioprosthetic heart valves can provide excellent hemodynamic and biomechanical performance in the short term, they are prone to calcification and cusp tears, among other failure modes, requiring reoperation and replacement.

Attempts have been made to use synthetic materials, such as polyurethane, among others, as a substitute for the biological tissue, to provide a more durable flexible leaflet prosthetic heart valve, herein referred to as a synthetic leaflet prosthetic heart valve (SLV). However, synthetic leaflet prosthetic heart valves have not become a valid heart valve replacement option since they suffer premature failure, due to, among other things, suboptimal design and lack of a durable synthetic material.

The leaflet moves under the influence of fluid pressure. In operation, the leaflets open when the upstream fluid pressure exceeds the downstream fluid pressure and close when the downstream fluid pressure exceeds the upstream fluid pressure. The leaflet free edges of the leaflets coapt under the influence of downstream fluid pressure closing the prosthetic heart valve to prevent downstream blood from flowing retrograde through the prosthetic heart valve.

Prosthetic heart valve durability under the repetitive loads of the leaflets opening and closing is dependent, in part, on the load distribution between the leaflet and the frame. Further, substantial load is encountered on the leaflet when in the closed position. Mechanical failure of the leaflet can arise, for example, at the mounting edge, where the flexible leaflet is supported by the relatively rigid frame. The repetitive loads of leaflet opening and closing leads to material failure by fatigue, creep or other mechanism, depending in part on the leaflet material. Mechanical failure at the mounting edge is especially prevalent with synthetic leaflets.

The durability of the valve leaflets is also a function of the character of bending by the leaflet during the opening-closing cycle. Small radius bends, creases and intersecting creases, can produce high stress zones in the leaflet. These high stress zones can cause the formation of holes and tears under repetitive loading.

Prosthetic heart valves may be delivered using surgical or transcatheter techniques. A surgical prosthetic heart valve is implanted into a patient using open-heart surgical techniques. The surgical prosthetic heart valve is usually manufactured to have a fixed diameter as opposed to a transcatheter prosthetic heart valve which is required to attain a range of diameters for access and delivery. The surgical prosthetic heart valve is usually provided with a sewing cuff about a perimeter of the prosthetic heart valve to allow for suturing to the native tissue orifice.

In addition to the prosthetic heart valve durability issues discussed above, the transcatheter prosthetic heart valve must also be able to withstand the handling and deployment stresses associated with being compressed and expanded.

A preferred shape of synthetic prosthetic heart valve leaflets has been described many times, but each is different from the others. The various three-dimensional shapes range from spherical or cylindrical to truncated conical intersections with spheres and an "alpharabola".

The shape most often described as preferable is modeled after the native human aortic valve. Though nature dictates the optimum shape for the native tissues to form a heart valve, we have discovered this is not true for synthetic materials; accordingly, the design specified in the current disclosure is instead intended to place the synthetic material under a minimized stress condition as compared to those based on copies of the native valve. This is partially accomplished through reduced buckling in the leaflet material.

SUMMARY

In accordance with an embodiment, a prosthetic valve comprises a leaflet frame having a generally tubular shape, an outer frame having a generally tubular shape, and a film. The term film as used herein generically refers to one or more of a membrane, composite material, or laminate. The coaxially disposed at least partially within the outer frame. The leaflet frame and outer frame are coupled at least in part by a contiguous portion of the film. The leaflet frame defines a plurality of leaflet windows, wherein the film defines a leaflet extending from each of the leaflet windows.

In accordance with another embodiment, a prosthetic valve comprises a leaflet frame having a generally tubular shape and an outer frame having a generally tubular shape. The leaflet frame and outer frame are coupled together by a contiguous portion of a film in which the leaflet frame is nested into the outer frame in a telescoping manner. The leaflet frame defines a plurality of leaflet windows, wherein the film defines a leaflet extending from each of the leaflet windows.

In accordance with an embodiment, a prosthetic valve comprises a leaflet frame having a generally tubular shape, an outer frame having a generally tubular shape, and film. The leaflet frame is coaxially disposed at least partially within the outer frame. The outer frame provides frame elements that overlay leaflet windows that are defined by the leaflet frame so as to provide structural support over the leaflet windows, as shown in FIGS. 1A-1B. The leaflet frame defines a plurality of leaflet windows, wherein the film defines a leaflet extending from each of the leaflet windows.

In accordance with an embodiment, a prosthetic valve comprises a leaflet frame having a generally tubular shape, an outer frame having a generally tubular shape, and film. The leaflet frame defines a plurality of leaflet windows. The film defines at least one leaflet extending from each of the leaflet windows. Each leaflet has substantially the shape of an isosceles trapezoid having two leaflet sides, a leaflet base and a free edge opposite the leaflet base. The two leaflet sides diverge from the leaflet base, wherein the leaflet base is substantially flat.

In accordance with other embodiments of the prosthetic valve, each leaflet includes a central region and two side regions on opposite sides of the central region. The central region is defined by a shape substantially that of an isosceles trapezoid defined by two central region sides, the leaflet base and the leaflet free edge. The two central region sides converge from the leaflet base. Each of the side regions has a shape substantially that of a triangle and each are defined by one of the central region sides, one of the leaflet sides, and the leaflet free edge.

In accordance with other embodiments of the prosthetic valve, each leaflet includes a central region and two side regions on opposite sides of the central region. The central region is defined by a shape substantially that of an isosceles triangle defined by two central region sides, the leaflet base and the leaflet free edge. The two central region sides converge from the leaflet base to the free edge. Each of the side regions has a shape substantially that of a triangle and each are defined by one of the central region sides, one of the leaflet sides, and the leaflet free edge. Each of the two side regions and the central region are substantially planar when the valve is in the closed position and under no pressure load.

In accordance with other embodiments of the prosthetic valve, the frame comprises a frame first end and a frame second end opposite the frame first end, the leaflet window having a shape determined, at least in part, by wrapping a two dimensional isosceles trapezoid onto the tubular shape of the frame, the isosceles trapezoid having a base and two sides that diverge from the base, and wherein a side from adjacent isosceles trapezoids meet at the frame second end.

In accordance with other embodiments of the prosthetic valve, the leaflets defining a shape of a trapezoid wherein frame elements bounds two sides, one side being a free edge, and the leaflet base being is a horizontal truncation bound only by the film.

In accordance with other embodiments of the prosthetic valve, the film defining at least one leaflet is coupled to an outer surface of the leaflet frame.

In accordance with other embodiments of the prosthetic valve, the film defining at least one leaflet is coupled to an inner surface of the leaflet frame.

In accordance with other embodiments of the prosthetic valve, the leaflet frame and outer frame are coupled at least in part by a contiguous portion of the film.

In accordance with other embodiments of the prosthetic valve, the outer frame provides frame elements that overlay leaflet windows that are defined by the leaflet frame so as to provide structural support over the leaflet windows.

In accordance with other embodiments of the prosthetic valve, the outer frame provides frame elements that overlay the leaflet windows that are defined by the leaflet frame, wherein the leaflet frame and outer frame present a substantially uniform geometric pattern of frame elements that act in concert so as to enable the frame assembly to compress and expand substantially uniformly when compressed and expanded for transcatheter applications.

In accordance with other embodiments of the prosthetic valve, the film is disposed between the leaflet frame and the outer frame.

In accordance with other embodiments of the prosthetic valve, the leaflet frame and outer frame are separated by the film and are not in contact with each other.

In accordance with other embodiments of the prosthetic valve, each leaflet has a substantially flat leaflet base.

In accordance with other embodiments of the prosthetic valve, the leaflet frame defines three interconnected leaflet windows having a substantially triangular shape.

In accordance with other embodiments the prosthetic valve comprises a leaflet frame having a generally tubular shape, an outer frame having a generally tubular shape, and a film. The leaflet frame is coaxially disposed at least partially within the outer frame. The leaflet frame and outer frame are coupled at least in part by a contiguous portion of the film.

In accordance with other embodiments of the prosthetic valve, the leaflet frame defines a plurality of leaflet windows, and the film defines a leaflet extending from each of the leaflet windows.

In accordance with other embodiments of the prosthetic valve, a leaflet window side of one leaflet window is interconnected with a leaflet window side of an adjacent leaflet window.

In accordance with other embodiments of the prosthetic valve, each leaflet has substantially the shape of an isosceles trapezoid having two leaflet sides, a leaflet base and a free edge opposite the leaflet base, wherein the two leaflet sides diverge from the leaflet base, wherein the leaflet base is substantially flat.

In accordance with other embodiments of the prosthetic valve, the leaflet window is defined by window frame elements corresponding to the leaflet sides and leaflet base, wherein the film is coupled to the window frame elements and extends across the leaflet window defining the leaflet.

In accordance with other embodiments of the prosthetic valve, the film extends across the leaflet window defining a bending region and a support region separated by a bending interface, wherein the leaflet bends within the bending region when cycled between an open and closed position, wherein the bending interface defines the leaflet base and sides having substantially the shape of an isosceles trapezoid.

In accordance with other embodiments of the prosthetic valve, the bending interface is collocated with the leaflet window sides.

In accordance with other embodiments of the prosthetic valve, the bending interface is collocated with the leaflet window sides and leaflet window base.

In accordance with other embodiments of the prosthetic valve, the bending interface is spaced apart from and not collocated with the leaflet window base.

In accordance with other embodiments of the prosthetic valve, the bending interface is spaced apart from and not collocated with the leaflet window sides and leaflet window base.

In accordance with other embodiments of the prosthetic valve, the bending interface is collocated with a portion of the leaflet window sides.

In accordance with other embodiments of the prosthetic valve, the bending interface defines the leaflet base and sides having the shape of an isosceles trapezoid.

In accordance with other embodiments of the prosthetic valve, the frame comprises a plurality of spaced apart leaflet windows each defining substantially an isosceles triangle interconnected by a base element, wherein each leaflet window side is defined by a side of one triangle and a side of an adjacent triangle, and wherein each leaflet window base is defined by the base element.

In accordance with other embodiments of the prosthetic valve, the frame comprises a base element and a plurality of spaced apart spade elements interconnected by the base element, wherein each leaflet window is defined by a side of one spade element and a side of an adjacent spade element, and wherein each leaflet window base is defined by the base element.

In accordance with other embodiments of the prosthetic valve, the frame comprises a plurality of spaced apart interconnected leaflet windows each defining substantially isosceles triangles, wherein each leaflet window side is defined by a side of one triangle and a side of an adjacent triangle, and wherein each leaflet window base is defined by the base element.

In accordance with other embodiments of the prosthetic valve, the prosthetic valve comprises a collapsed configuration and an expanded configuration for transcatheter delivery.

In accordance with other embodiments of the prosthetic valve, the leaflet is moveable between an open and closed position.

In accordance with other embodiments of the prosthetic valve, the leaflet comprises a polymeric film.

In accordance with other embodiments of the prosthetic valve, the leaflet comprises a laminate.

In accordance with other embodiments of the prosthetic valve, wherein the laminate has more than one layer of a fluoropolymer membrane.

In accordance with other embodiments of the prosthetic valve, the leaflet comprises a film having at least one fluoropolymer membrane layer having a plurality of pores and an elastomer present in substantially all of the pores of at least one layer of fluoropolymer membrane.

In accordance with other embodiments of the prosthetic valve, the film comprises less than about 80% fluoropolymer membrane by weight.

In accordance with other embodiments of the prosthetic valve, the elastomer comprises (per)fluoroalkylvinylethers (PAVE).

In accordance with other embodiments of the prosthetic valve, the elastomer comprises a copolymer of tetrafluoroethylene and perfluoromethyl vinyl ether.

In accordance with other embodiments of the prosthetic valve, the fluoropolymer membrane comprises ePTFE.

In accordance with other embodiments of the prosthetic valve, the leaflet frame and/or outer frame is defines a generally open pattern of apertures operable to allow the outer frame to be compressed and expanded between different diameters.

In accordance with other embodiments of the prosthetic valve, an aspect ratio of a length of the valve to an diameter of the valve is less than 1.

In accordance with other embodiments of the prosthetic valve, the valve is less than about 20 mm in length.

In accordance with other embodiments of the prosthetic valve, the leaflet frame and/or outer frame comprise a shape memory film.

In accordance with other embodiments of the prosthetic valve, the leaflet frame and/or outer frame comprises a metallic film.

In accordance with other embodiments of the prosthetic valve, in a collapsed configuration has a collapsed profile less than about 6 mm.

In accordance with other embodiments of the prosthetic valve, the valve is balloon expandable.

In accordance with other embodiments of the prosthetic valve, the film sandwiches the outer frame and the leaflet frame.

In accordance with an embodiment, a prosthetic valve comprises a plurality of leaflets, each leaflet having a shape substantially that of an isosceles trapezoid having two leaflet sides, a leaflet base, and a free edge opposite the leaflet base, wherein the two leaflet sides diverge from the leaflet base.

In accordance with another embodiment, a prosthetic valve comprises a plurality of leaflets, wherein, wherein each leaflet includes a central region and two side regions on opposite sides of the central region, wherein the central region is defined by a shape substantially that of an isosceles triangle defined by two central region sides, the leaflet base and the leaflet free edge, wherein the two central region sides converge from the leaflet base, and wherein each of the side regions have a shape substantially that of a triangle and each are defined by one of the central region sides, one of the leaflet sides, and the leaflet free edge.

In accordance with an embodiment, a prosthetic valve comprises a leaflet frame, an outer frame, and a film. The leaflet frame has a generally tubular shape defining a plurality of leaflet windows. The outer frame has a generally tubular shape. The leaflet frame is coaxially disposed at least partially within the outer frame. The leaflet frame and outer frame are coupled at least in part by a contiguous portion of the film. At least a portion of the contiguous portion of the film is contained between and coupling the leaflet frame and outer frame operable to prevent relative movement and contact therebetween. The film defines a leaflet extending from each of the leaflet windows.

In accordance with an embodiment, a prosthetic valve comprises and leaflet frame, and outer frame and a film. The leaflet frame has a generally tubular shape defining a plurality of leaflet windows. The outer frame has a generally tubular shape. The leaflet frame is coaxially disposed at least partially within the outer frame. The outer frame includes frame elements that overlay the leaflet windows that are defined by the leaflet frame in cooperative arrangement so as to provide structural support over the leaflet windows. The film defines a leaflet extending from each of the leaflet windows.

In accordance with an embodiment, a method of making a prosthetic valve, comprises: wrapping a first layer of film into a tubular form about a mandrel;

providing a leaflet frame having a generally tubular shape, the leaflet frame having a leaflet frame leaflet surface and a leaflet frame outer surface, the leaflet frame defining a plurality of leaflet windows having a window top; providing an outer frame having a generally tubular shape, the outer frame having an outer frame leaflet surface and an outer frame outer surface; placing the leaflet frame and the outer frame over the first layer of film with the leaflet frame and outer frame spaced apart from each other defining a bridge portion therebetween, the leaflet frame inner surface and the outer frame inner surface in contact with the first layer of film;

forming a second layer of film over the leaflet frame and the outer frame in contact with the leaflet frame outer surface and the outer frame outer surface; coupling the first layer of film and the second layer of film to each other and to the leaflet frame and the outer frame; cutting the first layer of film and the second layer of film across the window top within the leaflet window so as to define a leaflet free edge; masking with release material a portion of the film disposed in the leaflet window that defines the leaflet to prevent further bonding of the leaflet during subsequent processing steps; wrapping a third layer of film into a tubular form over the second layer of film and over the release material that is over the leaflet window, overlapping the leaflet frame, the outer frame, and over the bridge portion between the leaflet frame and outer frame; coupling the third layer of film and the second layer of film to each other;

removing the assembly from the mandrel; disposing coaxially and at least partially the leaflet frame into the outer frame, folding and overlapping at least partially the bridge portion so as to contain the bridge portion between the leaflet frame and the outer frame; placing the assembly back on the mandrel; coupling the bridge portion to itself and to the third layer of film adjacent the leaflet frame outer surface and the first layer adjacent the outer frame inner surface in nesting engagement.

Described embodiments are directed to an apparatus, system, and methods for valve replacement, such as cardiac valve replacement. More specifically, described embodiments are directed toward flexible leaflet valve devices in which the leaflets are divided into zones, each with a particular geometry.

In accordance with an embodiment, a prosthetic valve comprises a plurality of leaflets, each leaflet defining two side regions and a central region between the side regions, the central region having a shape that is different from that of the side regions.

In accordance with an embodiment, a prosthetic valve comprises a leaflet frame and a film. The leaflet frame has a generally tubular shape. The leaflet frame defines a plurality of leaflet windows wherein each of the leaflet windows includes two leaflet window sides, a leaflet window base, and a leaflet window top. The film being coupled to the leaflet frame and defining at least one leaflet extending from each of the leaflet windows, wherein each leaflet has substantially the shape of an isosceles trapezoid having two leaflet sides, a leaflet base and a free edge opposite the leaflet base, wherein the two leaflet sides diverge from the leaflet base, and wherein the leaflet base is substantially flat. The leaflet base is coupled to the window base and each of the two leaflet sides are coupled to one of the two window sides.

In accordance with an embodiment, a prosthetic valve comprises a plurality of leaflets. Each leaflet includes a central region and two side regions on opposite sides of the central region. The central region is defined by a shape substantially that of an isosceles triangle defined by two central region sides, the leaflet base and the leaflet free edge, wherein the two central region sides converge from the leaflet base, and wherein each of the side regions have a shape substantially that of a triangle and each are defined by one of the central region sides, one of the leaflet sides, and the leaflet free edge.

In accordance with an embodiment, a method of forming a prosthetic heart valve comprises providing a leaflet frame having a generally tubular shape, the leaflet frame defining a plurality of leaflet windows wherein each of the leaflet windows includes two leaflet window sides, a leaflet window base, and a leaflet window top; providing a film, and wrapping the film about the leaflet frame bringing more than one layer of the film into contact with additional layers of the film defining at least one leaflet extending from each of the leaflet windows, wherein each leaflet has substantially the shape of an isosceles trapezoid having two leaflet sides, a leaflet base and a free edge opposite the leaflet base, wherein the two leaflet sides diverge from the leaflet base, wherein the leaflet base is substantially flat; wherein the leaflet base is coupled to the window base and wherein each of the two leaflet sides are coupled to one of the two window sides providing a generally annular support structure; and bonding the layers of film to itself and to the leaflet frame.

In accordance with an embodiment, a method of forming a prosthetic heart valve comprises providing a leaflet frame having a generally tubular shape, the leaflet frame defining a plurality of leaflet windows, wherein each of the leaflet windows includes two leaflet window sides, a leaflet window base, and a leaflet window top; providing a film; wrapping the film about the leaflet frame bringing more than one layer of the film into contact with additional layers of the film defining at least one leaflet extending from each of the leaflet windows, wherein each leaflet has substantially the shape of an isosceles trapezoid having two leaflet sides, a leaflet base and a free edge opposite the leaflet base, wherein the two leaflet sides diverge from the leaflet base, wherein the leaflet base is substantially flat; wherein the leaflet base is coupled to the window base and wherein each of the two leaflet sides are coupled to one of the two window sides providing a generally annular support structure; and bonding the layers of film to itself and to the leaflet frame.

Described embodiments are directed to an apparatus, system, and methods for valve replacement, such as cardiac valve replacement. More specifically, described embodiments are directed toward flexible leaflet valve devices in which a truncated segment at the base of the leaflet is present at or adjacent to the intersection with the frame.

In accordance with an embodiment, a prosthetic valve comprises a leaflet frame, a plurality of leaflets that are coupled to the leaflet frame, where each leaflet has a free edge and a base. The base of each leaflet is truncated in which the leaflet in cross section shows a line in an alpha plane onto the leaflet frame.

In accordance with an embodiment, a prosthetic valve comprises a frame having a generally tubular shape with attached film. The frame defines a plurality of leaflet windows. The film defines at least one leaflet extending from each of the leaflet windows. Each leaflet two leaflet sides, a planar central zone, a leaflet base and a free edge opposite the leaflet base. The two leaflet sides diverge from the leaflet base.

In accordance with an embodiment, a prosthetic valve comprises a leaflet frame, a plurality of leaflets that are coupled to the leaflet frame, where each leaflet has a free edge and a base. Each leaflet has a planar zone in a central portion, wherein the planar zone is substantially planar. The planar zone defines a shape having an area, wherein the area is larger nearer the base than the free edge.

In accordance with an embodiment, a prosthetic heart valve comprises a leaflet frame having a generally tubular shape with attached film. The leaflet frame defines a plurality of leaflet windows. The film defines at least one leaflet extending from each of the leaflet windows. Each leaflet attachment zone on the leaflet frame has substantially the shape of an isosceles trapezoid having two leaflet sides, a leaflet base and a leaflet free edge opposite the leaflet base. The two leaflet sides diverge from the leaflet base, wherein the leaflet base is substantially flat.

In accordance with other embodiments of the prosthetic heart valve, each leaflet attachment zone on the leaflet frame includes a central region and two side regions on opposite sides of the central region. The central region of the attachment zone on the leaflet frame is defined by a shape substantially that of an isosceles trapezoid defined by two central region sides, the leaflet base and the leaflet free edge. The two central region sides of the attachment zone on the leaflet frame converge from the leaflet base. Each of the side regions of the attachment zone on the leaflet frame has a shape substantially that of a triangle and each are defined by one of the central region sides, one of the leaflet sides, and the leaflet free edge.

In accordance with other embodiments of the prosthetic heart valve, each leaflet attachment zone on the leaflet frame includes a central region and two side regions on opposite sides of the central region. The central region of the attachment zone on the leaflet frame is defined by a shape substantially that of an isosceles triangle defined by two central region sides, the leaflet base and the leaflet free edge. The two central region sides converge from the leaflet base to the leaflet free edge. Each of the side regions of the attachment zone on the leaflet frame has a shape substantially that of a triangle and each are defined by one of the central region sides, one of the leaflet sides, and the leaflet free edge In accordance with other embodiments of the prosthetic heart valve, the leaflet frame comprises a leaflet frame first end and a leaflet frame second end opposite the leaflet frame first end, the leaflet window having a shape determined, at least in part, by wrapping a two dimensional isosceles trapezoid pattern onto the tubular shape of the leaflet frame, the isosceles trapezoid pattern having a base and two sides that diverge from the base, and wherein a side from adjacent isosceles trapezoids meet at the leaflet frame second end.

In accordance with other embodiments of the prosthetic heart valve, the leaflets defining a shape of a trapezoid wherein frame elements bounds two sides, one side being a leaflet free edge, and the leaflet base being is a horizontal truncation bound only by the film.

In accordance with an embodiment, a prosthetic heart valve comprises a plurality of leaflets, each leaflet attachment zone on the leaflet frame having a shape substantially that of an isosceles trapezoid having two leaflet sides of the attachment zone on the leaflet frame, a leaflet base, and a leaflet free edge opposite the leaflet base, wherein the two leaflet sides diverge from the leaflet base.

In accordance with another embodiment, a prosthetic heart valve comprises a plurality of leaflets, wherein, wherein each leaflet attachment zone on the leaflet frame includes a central region and two side regions on opposite sides of the central region, wherein the central region is defined by a shape substantially that of an isosceles triangle defined by two central region sides, the leaflet base and the leaflet free edge, wherein the two central region sides converge from the leaflet base, and wherein each of the side regions of the attachment zone on the leaflet frame have a shape substantially that of a triangle and each are defined by one of the central region sides, one of the leaflet sides, and the leaflet free edge.

BRIEF DESCRIPTION OF THE DRAWINGS

The accompanying drawings are included to provide a further understanding of the present disclosure and are incorporated in and constitute a part of this specification, illustrate embodiments described herein, and together with the description serve to explain the principles discussed in this disclosure.

FIG. 5A is a cross-sectional view of an embodiment of the valve during manufacture;

FIG. 5B is a cross-sectional view of the leaflet frame and the outer frame as nested together, in accordance with the embodiment of FIG. 5A;

DETAILED DESCRIPTION

Figure 1A:
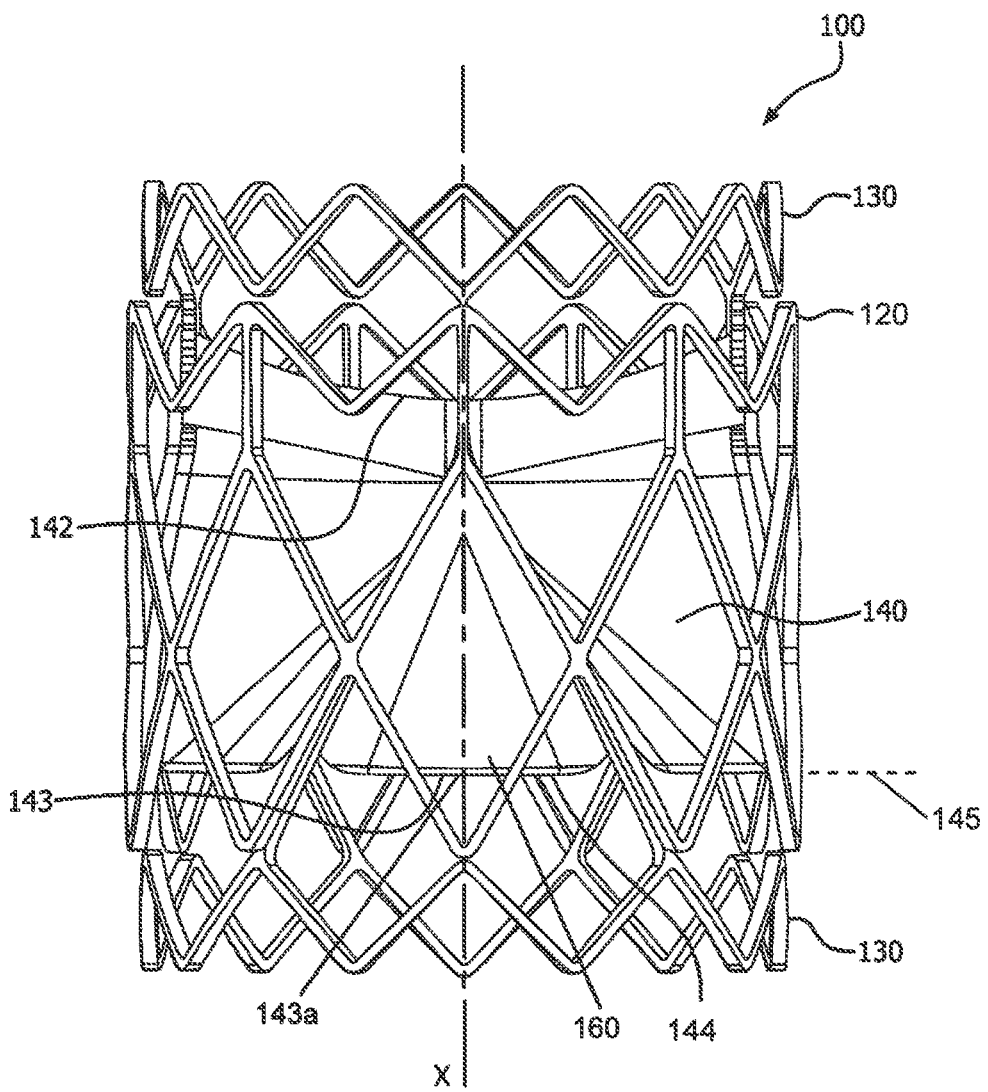
FIG. 1A is a side view of an embodiment of a prosthetic heart valve.

Persons skilled in the art will readily appreciate that various aspects of the present disclosure can be realized by any number of methods and apparatus configured to perform the intended functions. Stated differently, other methods and apparatuses can be incorporated herein to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Although the embodiments herein may be described in connection with various principles and beliefs, the described embodiments should not be bound by theory. For example, embodiments are described herein in connection with prosthetic heart valves, more specifically cardiac prosthetic heart valves. However, embodiments within the scope of this disclosure can be applied toward any heart valve or mechanism of similar structure and/or function. Furthermore, embodiments within the scope of this disclosure can be applied in non-cardiac applications.

The term leaflet as used herein in the context of prosthetic heart valves is a component of a one-way valve wherein the leaflet is operable to move between an open and closed position under the influence of a pressure differential. In an open position, the leaflet allows blood to flow through the prosthetic heart valve. In a closed position, the leaflet substantially blocks retrograde flow through the prosthetic heart valve. In embodiments comprising multiple leaflets, each leaflet cooperates with at least one neighboring leaflet to block the retrograde flow of blood. The pressure differential in the blood is caused, for example, by the contraction of a ventricle or atrium of the heart, such pressure differential typically resulting from a fluid pressure building up on one side of the leaflets when closed. As the pressure on an inflow side of the prosthetic heart valve rises above the pressure on the outflow side of the prosthetic heart valve, the leaflets open and blood flows therethrough. As blood flows through the prosthetic heart valve into a neighboring chamber or blood vessel, the pressure on the inflow side equalizes with the pressure on the outflow side. As the pressure on the outflow side of the prosthetic heart valve rises above the blood pressure on the inflow side of the prosthetic heart valve, the leaflet returns to the closed position generally preventing retrograde flow of blood through the prosthetic heart valve.

The term membrane as used herein refers to a sheet of material comprising a single composition, such as, but not limited to, expanded fluoropolymer.

The term composite material as used herein refers to a combination of a membrane, such as, but not limited to, expanded fluoropolymer, and an elastomer, such as, but not limited to, a fluoroelastomer. The elastomer may be imbibed within a porous structure of the membrane, coated on one or both sides of the membrane, or a combination of coated on and imbibed within the membrane.

The term laminate as used herein refers to multiple layers of membrane, composite material, or other materials, such as elastomer, and combinations thereof.

The term film as used herein generically refers to one or more of the membrane, composite material, or laminate.

The term leaflet window is defined as that space that a leaflet frame defines from which a leaflet extends. The leaflet may extend from leaflet frame elements or adjacent to and spaced apart therefrom.

The term frame element as used herein refers to any portion of a leaflet frame or outer frame, such as, but not limited to, those individual portions that define a leaflet window or aperture.

The term attachment zone as used herein refers to the portion of the film that is attached to something so as to define the shape of the leaflet. The attachment zone may be, such as, but not limited to, that portion of the film that is coupled to the frame elements that define the leaflet window. The attachment zone may also be, such as, but not limited to, that portion of the film that is coupled to another film at a location that is not directly adjacent to a frame element.

The terms native heart valve orifice and tissue orifice refer to an anatomical structure into which a prosthetic heart valve may be placed. Such anatomical structure includes, but is not limited to, a location wherein a cardiac valve may or may not have been surgically removed. It is understood that other anatomical structures that may receive a prosthetic heart valve include, but are not limited to, veins, arteries, ducts and shunts. Although reference is made herein to replacing a native heart valve with a prosthetic heart valve, it is understood and appreciated that a valve orifice or implant site may also refer to a location in a synthetic or biological conduit that may receive a valve for a particular purpose, and therefore the scope of the embodiments provided herein is not limited to heart valve replacement.

As used herein, "couple" means to join, connect, attach, adhere, affix, or bond, whether directly or indirectly, and whether permanently or temporarily.

Figure 3A:
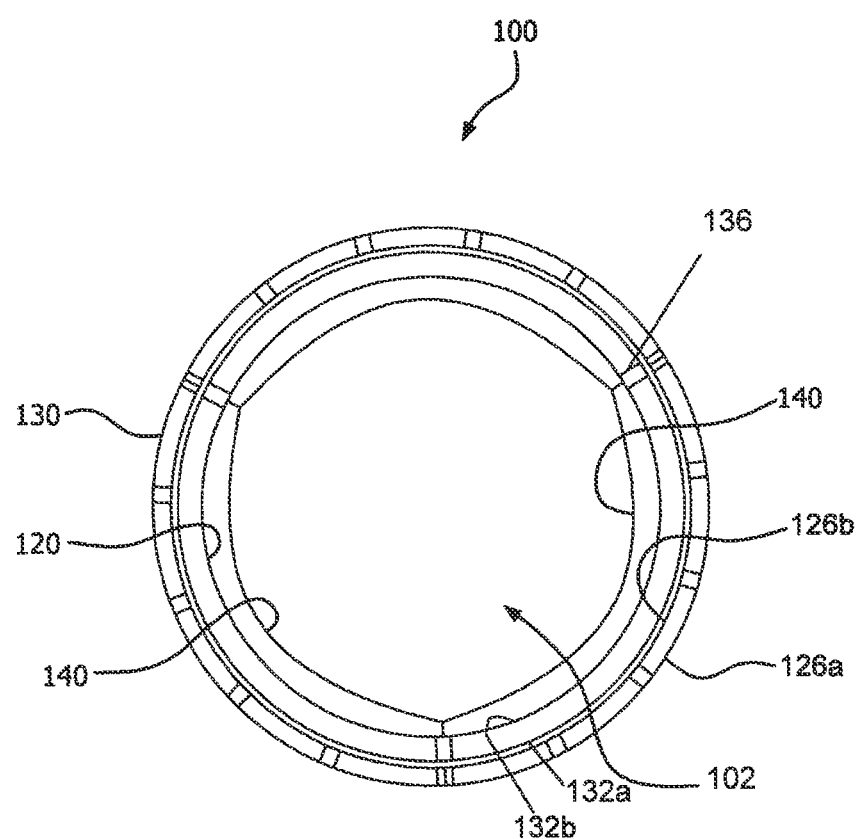
FIG. 3A is an axial or top view of the embodiment of the prosthetic heart valve of FIG. 1A in an open configuration.
Figure 3B:
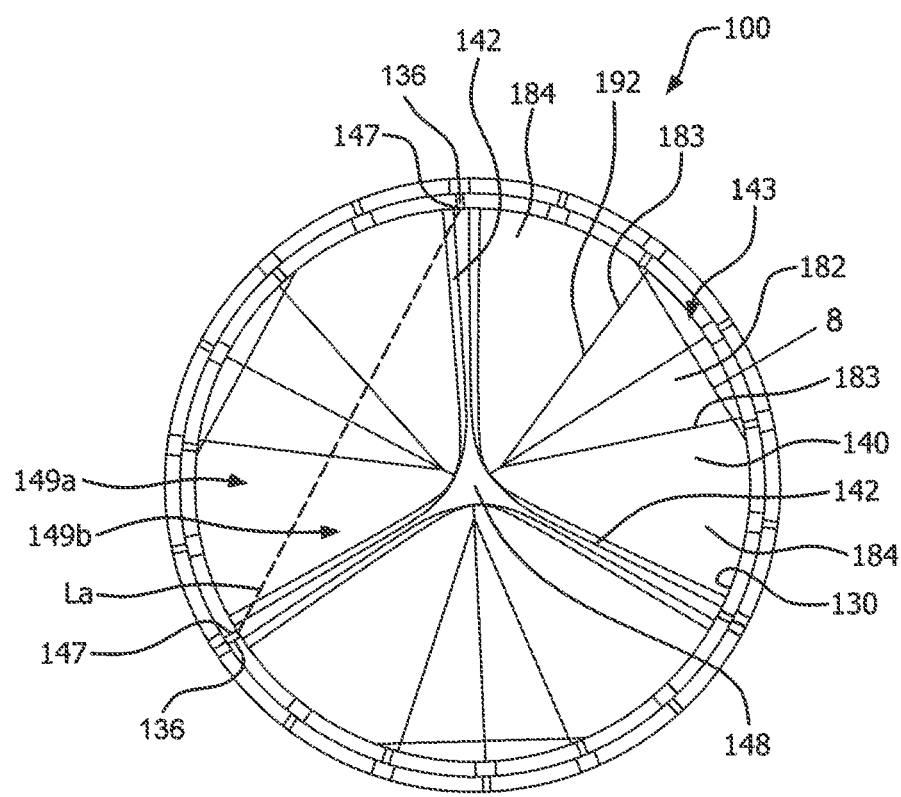
FIG. 3B is an axial or top view of the embodiment of the prosthetic heart valve of FIG. 1A in a closed configuration.

As used herein, truncated or truncation refers to the sectioning of a three-dimensional body with a plane reducing the size of the body. Referring to FIGS. 1A and 3B, a truncation zone is that area of the leaflet that may be truncated by a truncation plane intersecting the alpha plane so as to define an attachment line, i.e., a line of attachment, of the leaflet base.

Embodiments herein include various apparatus, systems, and methods for a prosthetic heart valve suitable for surgical and transcatheter placement, such as, but not limited to, cardiac valve replacement. The prosthetic heart valve is operable as a one-way valve wherein the prosthetic heart valve defines a valve orifice into which leaflets open to permit flow and close so as to occlude the valve orifice and prevent flow in response to differential fluid pressure.

Embodiments provided herein are related to controlled leaflet opening. The durability of the prosthetic heart valve leaflets is largely controlled by the character of bending exhibited by the leaflet during the opening-closing cycle. Small radius bends, creases and particularly intersecting creases, can produce high stress zones in the leaflet. These high stress zones can cause the formation of holes and tears under repetitive loading.

Controlled bending is of particular importance in thin, high-modulus synthetic leaflets, since the bending in these materials tends to be cellophane-like. If the leaflet bending character is uncontrolled, not only do creases form, but crease intersections lead to formation of large three dimensional structures that oppose bending and slow down the leaflet motion, both in opening and closing: in order to avoid this, the sequence of opening of the parts of the leaflet must be controlled.

Controlled bending is achieved through a particular frame shape, in accordance with embodiments. The frame shape dictates the leaflet attachment perimeter, which further dictates leaflet movement.

Embodiments provided herein present advancement in prosthetic heart valve technology related to, but not limited to, mechanic and biological performance advantages. In accordance with some embodiments presented herein, a prosthetic heart valve comprises two frames, a leaflet frame and an outer frame, that are coupled together by a contiguous film in which a leaflet frame is nested into an outer frame in a telescoping manner, wherein there is no chance for the prosthetic heart valve to leak between the leaflet frame and the outer frame.

In accordance with some embodiments presented herein, a prosthetic heart valve comprises two frames; a leaflet frame and an outer frame. The film that comprises the leaflet may be coupled to the inner surface of the leaflet frame. In some other embodiments, the film that comprises the leaflet is contained between the leaflet frame and the outer frame and extends through a leaflet window defined by the leaflet frame. The leaflet, therefore, is significantly prevented from peeling or delaminating as it is contained between the leaflet frame and outer frame, as compared to where the leaflets are only coupled to the inner surface of the leaflet frame.

In accordance with some embodiments presented herein, a prosthetic heart valve comprises two frames; a leaflet frame and an outer frame. The leaflet frame and the outer frame are separated from each other by a film. In other words, there is a metal to polymer to metal interconnection, wherein there is no metal to metal contact between the leaflet frame and the outer frame.

In accordance with some embodiments presented herein, a prosthetic heart valve comprises two frames; a leaflet frame and an outer frame. The leaflet frame is nested within the outer frame, wherein the leaflet frame and outer frame cooperate to provide relatively high resistance to flat plate compression, among other things. In accordance with some embodiments, the outer frame provides frame elements that overlay the leaflet windows that are defined by the leaflet frame so as to provide structural support over the leaflet windows. In accordance with some embodiments, the outer frame provides frame elements that overlay the leaflet windows that are defined by the leaflet frame so as to prevent tissue from extending into the leaflet windows when implanted. In accordance with some embodiments, the outer frame provides frame elements that overlay the leaflet windows that are defined by the leaflet frame and act in concert so as to allow the frame assembly to compress and expand uniformly for transcatheter embodiments.

In accordance with some embodiments presented herein, a prosthetic valve comprises two frames; a leaflet frame and an outer frame. The leaflet frame defines leaflet windows that define, in part, the shape of the leaflets. In some embodiments the leaflet comprises a flat base, wherein the leaflet bends from the base towards the leaflet free edge with minimal creasing and fluttering. In some embodiments the leaflet comprises a flat base, that, among other things, that provides for one or more of a shorter valve length, substantially prevents blood stagnation and pooling and encourages washing at the base, as compared to leaflets having a rounded base.

In accordance with some embodiments presented herein, a prosthetic valve comprises two frames; a leaflet frame and an outer frame. The leaflet frame defines leaflet windows from which the leaflets extend. The leaflets are defined by the intersection of films that form an overlapping zone so as to define, at least in part, the leaflet base and/or the leaflet sides.

The length of a leaflet heart valve is dictated by the angle the leaflet makes with respect to the enclosing frame. A longer leaflet has a shallower angle with respect to the frame. A shorter leaflet has a steeper angle with respect to the frame. A longer leaflet leads to better performance than a shorter leaflet. For most applications however, only a short valve can fit into the recipient location. Thus the valve designer is presented with a dilemma. In the instant embodiments, leaflet designs are provided that provide for good performance with a short leaflet, thus allowing short heart valves.

Embodiments provided herein place the synthetic materials under a minimized stress condition as compared to those based on copies of the native valve. This is partially accomplished through reduced buckling in the leaflet material.

Embodiments provided herein address controlled leaflet opening. The durability of the valve leaflets is largely controlled by the character of bending exhibited by the leaflet during the opening-closing cycle. Small radius bends, creases and particularly intersecting creases, can produce high stress zones in the leaflet. These high stress zones can cause the formation of holes and tears under repetitive loading. Embodiments provided herein provide a feature of leaflet shape so as to minimize crease formation, which is of particular importance in thin, high-modulus leaflets, since the bending in these materials tends to be cellophane-like. If the leaflet bending is unrestricted, not only do creases form, but crease intersections lead to formation of large three dimensional structures that oppose bending and slow down the leaflet motion, both in opening and closing. Embodiments provided herein control leaflet opening and provide minimization of crease formation provided by an inclusion of a planar zone in the leaflet.

Prosthetic Heart Valve

Figure 16A:
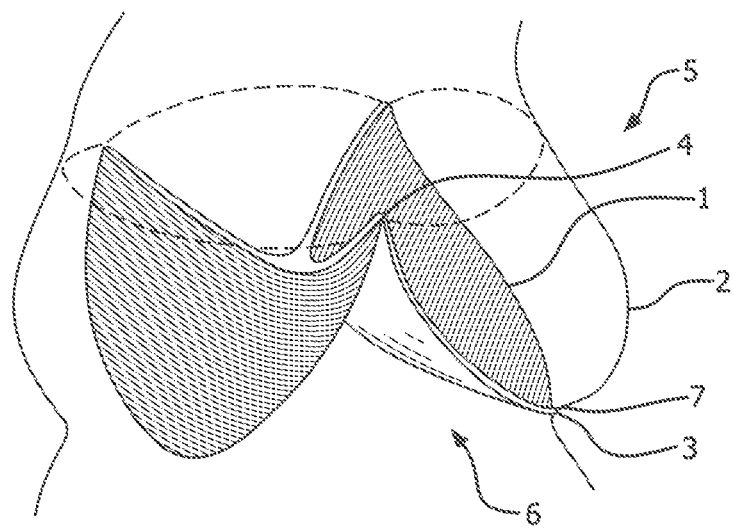
FIG. 16A is a representation of an aortic valve.
Figure 16B:
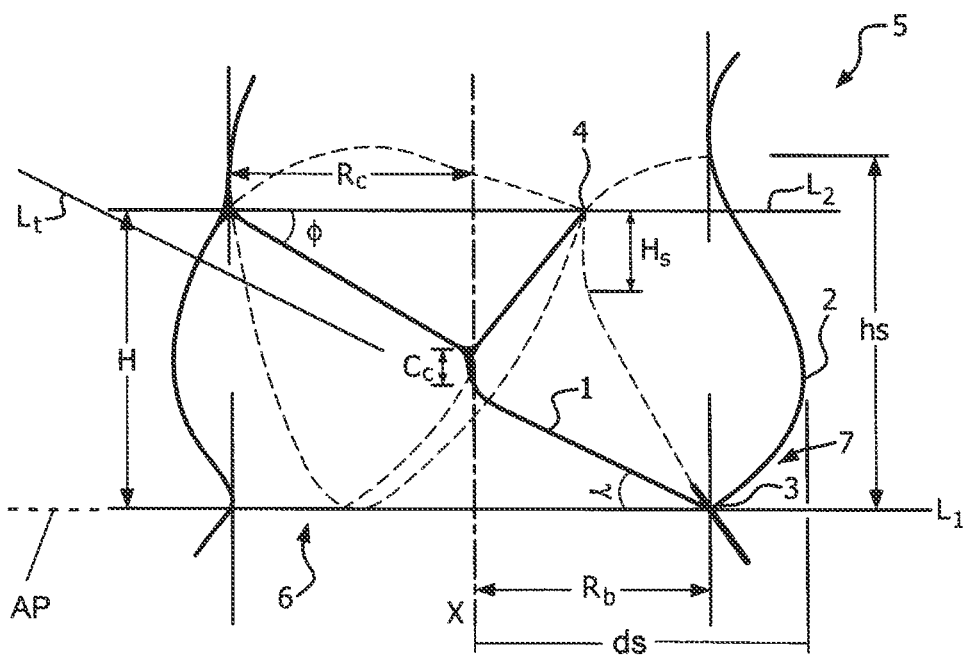
FIG. 16B is a cross-section of the aortic valve of FIG. 16A showing the angles associated with a leaflet heart valve.

FIG. 16A is a sketch of an aortic valve 5. The leaflets 1 are coupled to the aortic root 2 at the leaflet base 3. FIG. 16B is a cross-section of the aortic valve of FIG. 16A showing the angles associated with a leaflet 1 of the aortic valve 5. FIG. 16B illustrates the relationship between the leaflets 1 and a first horizontal line L1 extending through the leaflet base 3 at an attachment point 7, and a second horizontal line L2 extending through the tops 4 of the commissure. In FIG. 16B, the aortic valve 5 is oriented in a position with a valve axis X being vertical, the inflow edge 6 is pointed downward, with the leaflets 1 in the closed position. The attachment angle alpha ($\alpha$) is defined as the angle between the tangent line Lt extending from the center of the leaflet base 3 of the leaflet 1 at the attachment point 7 and the first horizontal line L1 extending through the leaflet base 3 at the attachment point 7, as shown in FIG. 16A.

Referring to FIG. 16B: Rb is the radius of the base, Rc is the radius of the commissures, H is the valve height, alpha is the bottom surface angle of the leaflet, phi is the free edge angle of the leaflet, Hs is the height of the commissures, and Cc is the coaptation height.

It is understood that leaflets 1 may exhibit a concave, straight, or convex shape in an axial cross-section through the center of the leaflet base 3 of the leaflet 1 at the attachment point 7. For the sake of clarity and simplification of description of the embodiments presented herein and not limited thereto, the geometry of a leaflet 1 is described as having, in an axial cross-section through the center of the leaflet base 3 of the leaflet 1 at the attachment point 7, the tangent line Lt that defines a as a straight line.

Embodiments provided herein provide a solution to the tension between desiring a small alpha angle to have a short valve and a larger alpha angle resulting in longer leaflets for better leaflet bending behavior. Embodiments provided herein provide a larger alpha angle while reducing valve length, by providing a leaflet that wherein the leaflet base 3 is truncated, providing a relatively flat leaflet base 143.

In accordance with embodiments herein, the attachment angle alpha (α) of a given valve configuration is preserved as the leaflet height is reduced. This is accomplished by redefining the base of the leaflet not as an attachment point 3 as for the generally parabolic leaflet shape as shown in FIG. 1A, but as an attachment line 8 as shown in FIG. 3B, that is parallel to the horizontal line in the valve cross sectional plane perpendicular to the valve axis X at the leaflet base 143 of the leaflet 140.

As a way to visualize embodiments provided herein, referring to FIG. 16B, the first horizontal line L1 extends through the leaflet base 3a as it moves perpendicular along the valve axis X towards the commissure tops 4. A plane containing the first horizontal line L1 and perpendicular to the valve axis, referred to as the alpha plane, intersects the leaflet frame 140 of FIG. 1A along a line. Wherein the leaflet base 7 is truncated by the alpha plane, wherein the attachment point 3 of the leaflet base 7 becomes an attachment line 144, that is, a line of attachment rather than a point, of the leaflet base 143 as shown in FIGS. 1A and 3B.

Referring to FIG. 3B, an apex line La is indicated connecting the apices 147 of the leaflets 140. The apex line La divides the leaflet 140 into a first region 149a adjacent the leaflet frame 130, and a second region 149b adjacent the leaflet free edge. The first region 149a defines a truncated zone. The truncated zone is located on the lower section of the leaflet 140 adjacent the leaflet base 143. Referring to FIGS. 1A and 3B, the truncation zone is that area of the leaflet 140 that may be truncated by a truncation plane intersecting the alpha plane so as to define an attachment line 144, i.e., a line of attachment, of the leaflet base 143.

Figure 1B:
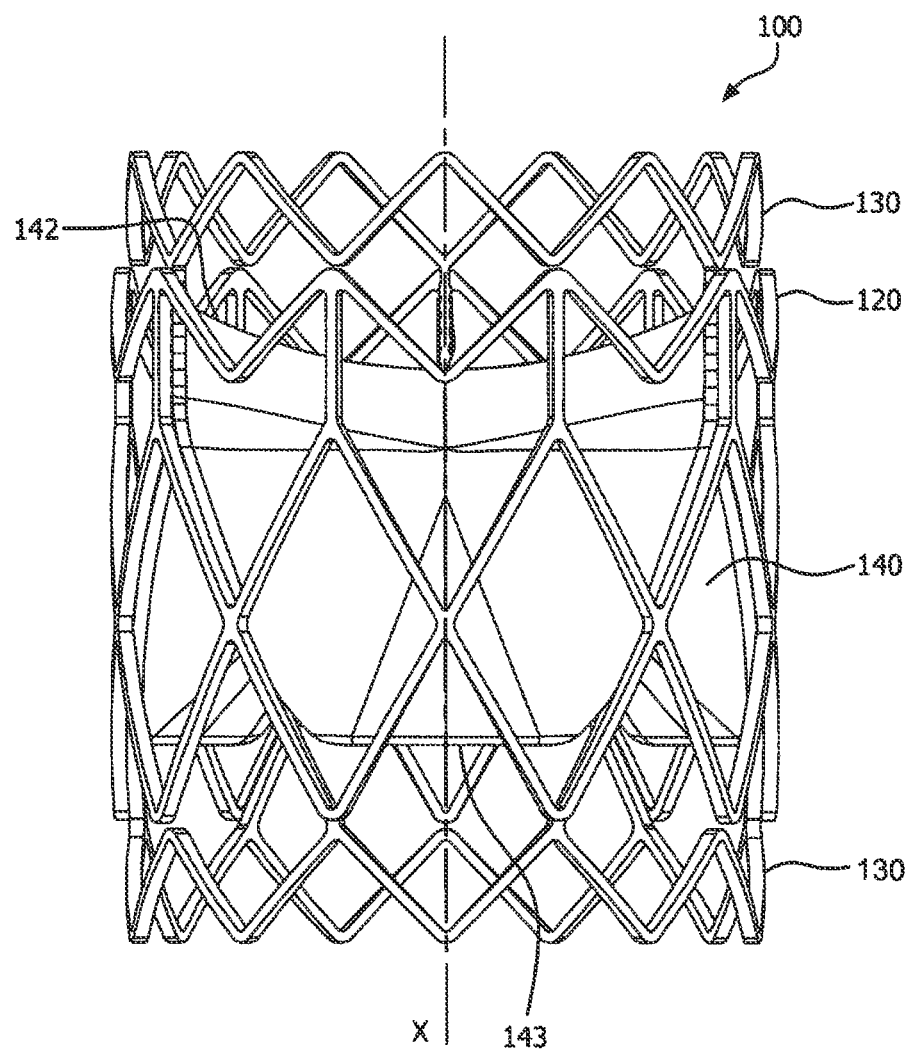
FIG. 1B is a side view of the embodiment of the prosthetic heart valve of FIG. 1A that is partially rotated about the axis X.
Figure 1C:
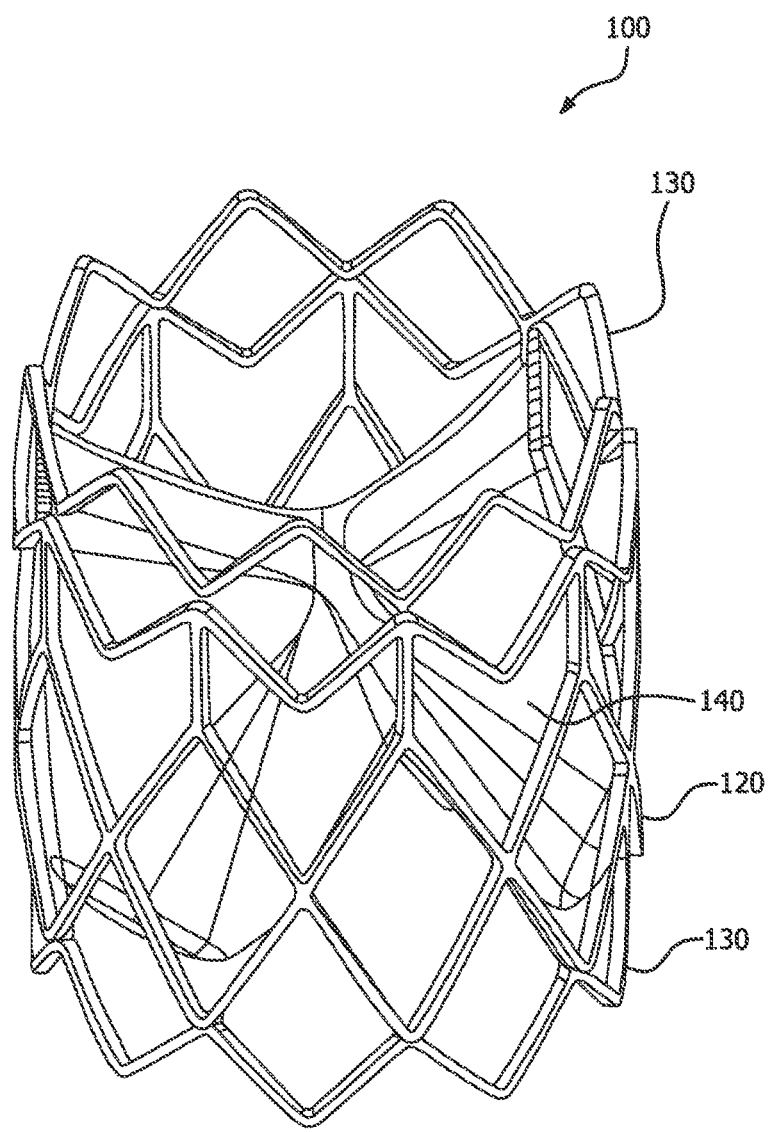
FIG. 1C is a perspective view of the embodiment of the prosthetic heart valve of FIG. 1A.
Figure 2A:
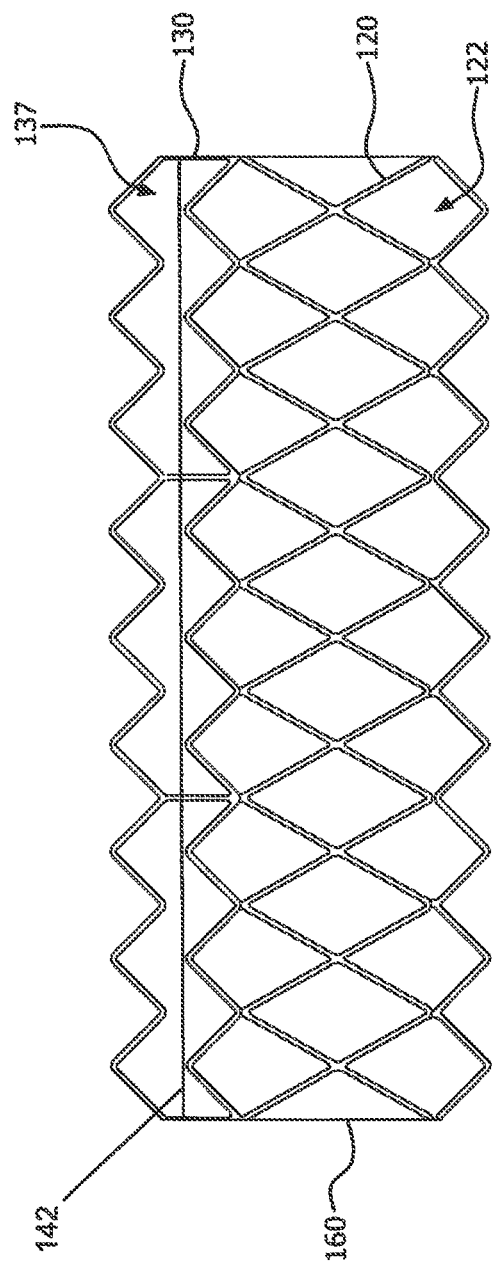
FIG. 2A is a representation of the embodiment of the prosthetic heart valve of FIG. 1A unrolled to a flat orientation.
Figure 2B:
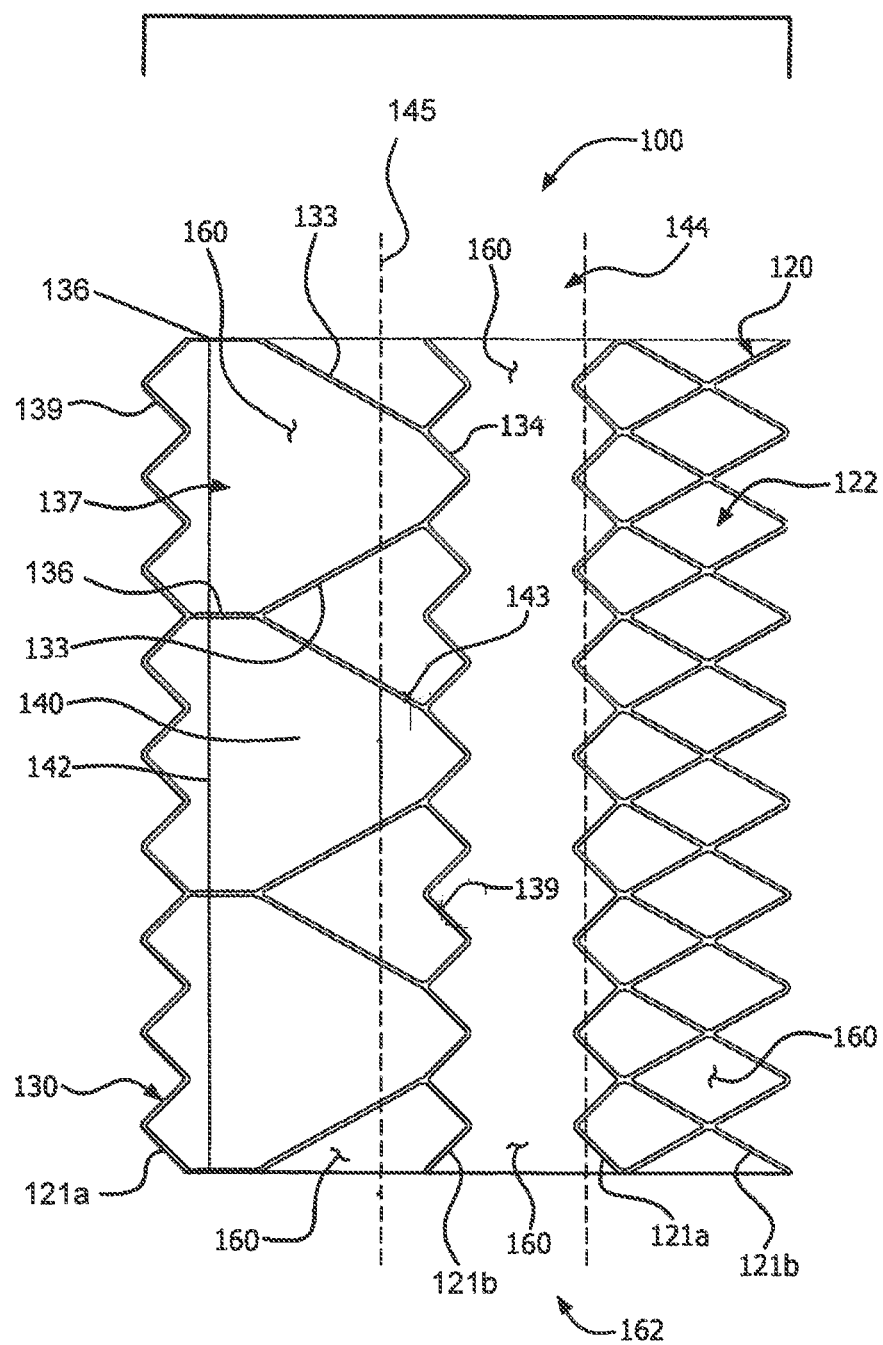
FIG. 2B is an exploded representation of the embodiment of the prosthetic heart valve of FIG. 1A unrolled to a flat orientation.

FIG. 1A is a side view of a prosthetic heart valve 100, in accordance with an embodiment. FIG. 1B is also a side view of the prosthetic heart valve 100 of FIG. 1A rotated 60 degrees about the longitudinal axis X. FIG. 1C is a perspective view of the prosthetic heart valve 100 of FIG. 1A. FIG. 2A is a side view of the prosthetic heart valve 100 of FIG. 1A wherein the prosthetic heart valve 100 has been longitudinally cut and laid open to better illustrate the elements of the generally tubular-shaped prosthetic heart valve 100. FIG. 2B is an exploded view of the embodiment of FIG. 2A. FIGS. 3A and 3B are axial views of the prosthetic heart valve 100 of FIG. 1A in an open and closed configuration, respectively. In FIG. 3B the leaflets 140 are shown slightly open to better show the features but it is understood that a fully closed prosthetic heart valve 100 will have the leaflet free edges 142 of the leaflets 140 coming together to coapt under the influence of downstream fluid pressure which results in closing the valve to prevent downstream blood from flowing retrograde through the valve.

The valve 100 comprises an outer frame 120, a leaflet frame 130, and a film 160 covering the outer frame 120 and leaflet frame 130, coupling the outer frame 120 to the leaflet frame 130, and defining leaflets 140. The embodiment of valve 100 is discussed further related to a transcatheter valve that may be compressed and re-expanded. It is understood that the embodiment of valve 100 is also applicable to a surgical valve by the addition of a sewing cuff 170 as shown in FIG. 4B. Leaflet frame and outer frame configurations related to surgical valve only embodiments where the valves have a fixed diameter, will be discussed in other embodiments later in this disclosure.

In accordance with an embodiment, a prosthetic valve comprises a leaflet frame 130 having a generally tubular shape, an outer frame 120 having a generally tubular shape, and film 160. The leaflet frame 130 is coaxially disposed at least partially within the outer frame 120. The outer frame 120 provides frame elements that overlay leaflet windows that are defined by the leaflet frame 130 so as to provide structural support over the leaflet windows, as shown in FIGS. 1A-1B. The leaflet frame 130 defines a plurality of leaflet windows, wherein the film 160 defines a leaflet extending from each of the leaflet windows.

11A is a side view of a prosthetic heart valve 200, in accordance with an embodiment. FIG. 11B is a perspective view of the prosthetic heart valve 200 of FIG. 1A. The prosthetic heart valve 200 comprises a leaflet frame 130f and film 160 that defines leaflets 140. In FIGS. 3B and 11D, the leaflets 140 are shown slightly open to better show the features but it is understood that a fully closed prosthetic heart valve 200 will have the leaflet free edges 142 of the leaflets 140 coming together to coapt under the influence of downstream fluid pressure which results in closing the valve to prevent downstream blood from flowing retrograde through the valve. The term "frame element" as used herein refers to any portion of the leaflet frame 130, such as, but not limited to, those individual portions that define a leaflet window 137. The leaflet frame first end 131a further comprises commissure posts 136 extending from an apex of the leaflet frame elements defining substantially a triangle.

Figure 8A:
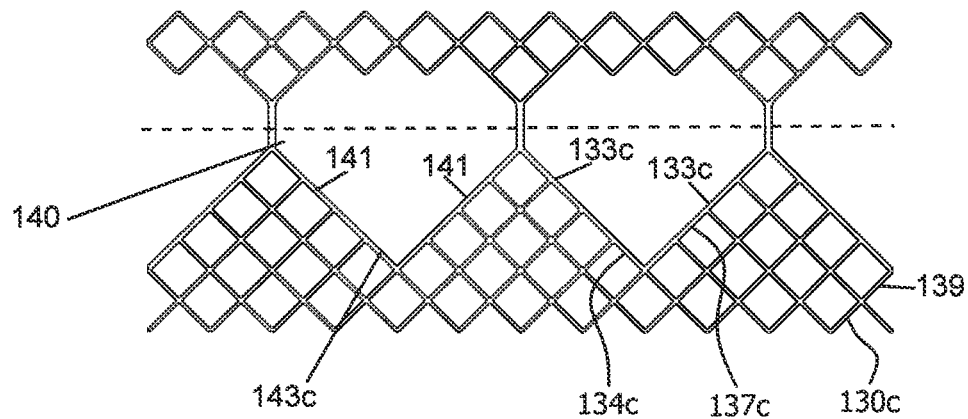
FIG. 8A is an embodiment of a leaflet frame unrolled to a flat orientation.
Figure 8B:
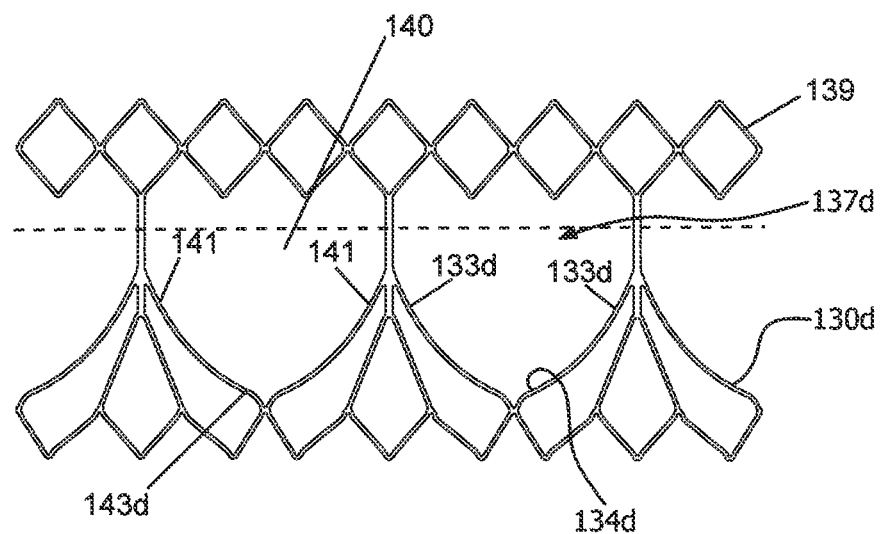
FIG. 8B is an embodiment of a leaflet frame unrolled to a flat orientation.
Figure 8C:
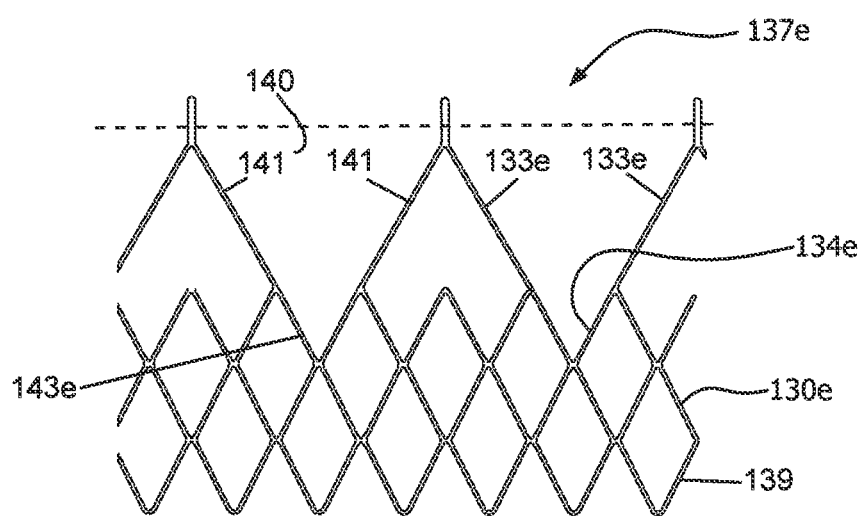
FIG. 8C is an embodiment of a leaflet frame unrolled to a flat orientation.
Figure 8D:
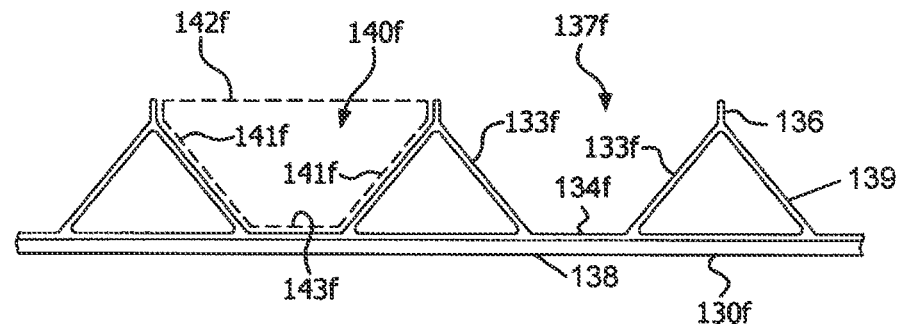
FIG. 8D is an embodiment of a leaflet frame unrolled to a flat orientation.
Figure 11A:
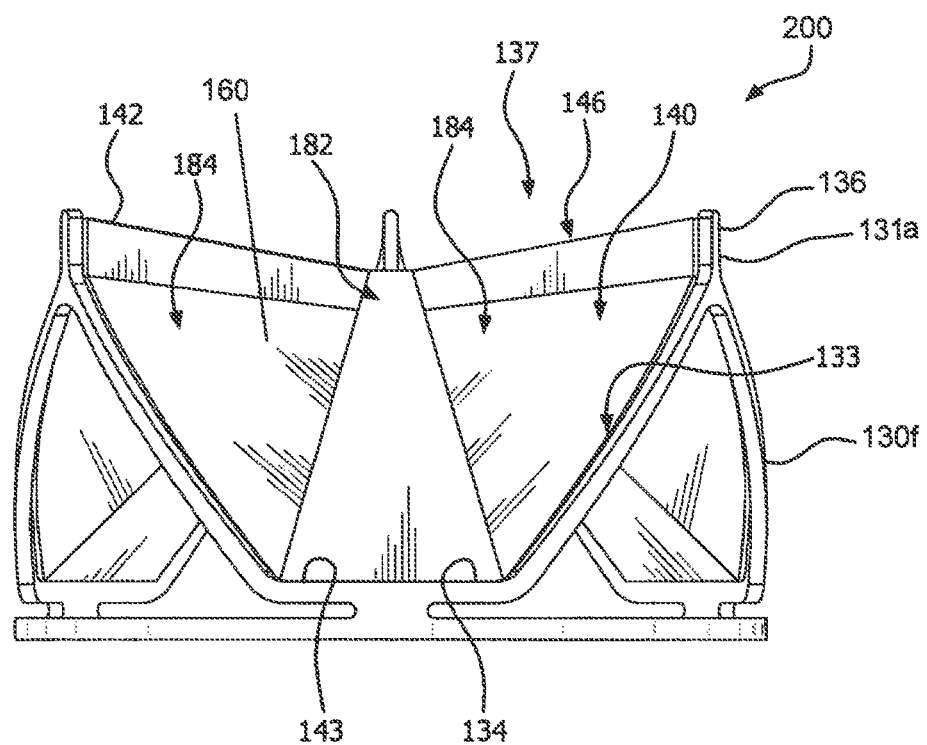
FIG. 11A is a side view of an embodiment of a prosthetic heart valve.
Figure 11B:
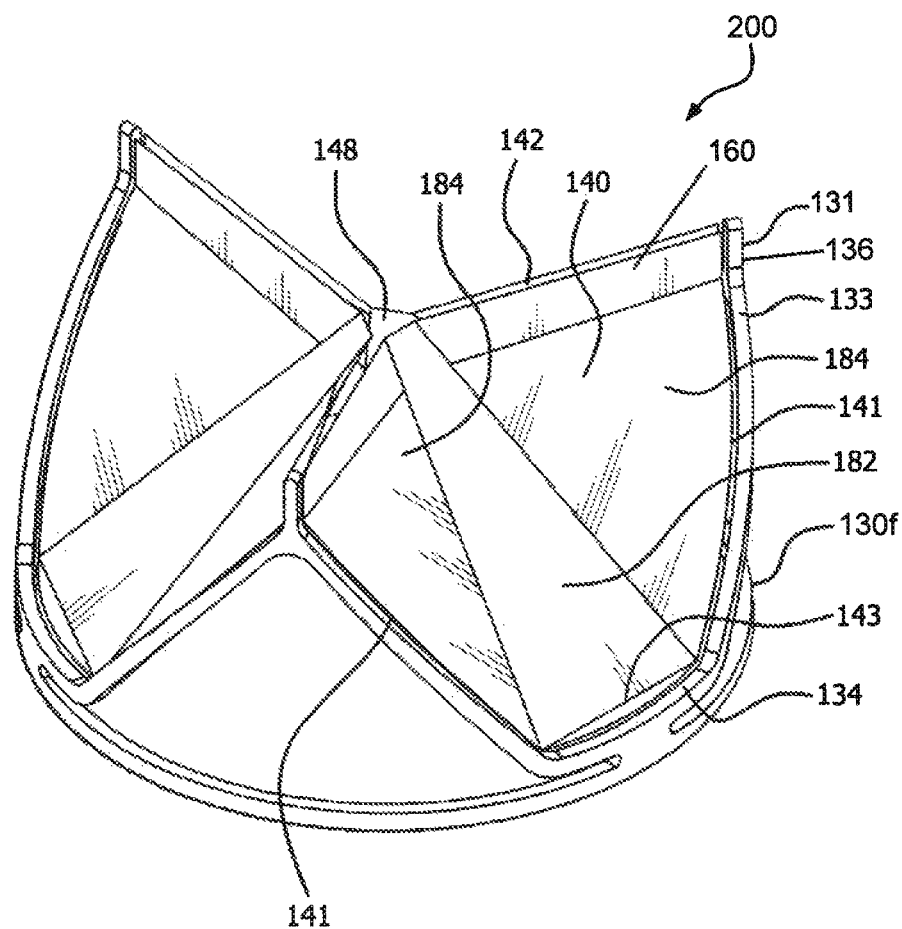
FIG. 11B is a perspective view of the embodiment of the prosthetic heart valve of FIG. 11A.

FIG. 8D is a side view of the leaflet frame 130f of the prosthetic heart valve 200 of FIGS. 11A and 11B wherein the leaflet frame 130f has been longitudinally cut and laid open to better illustrate the elements of the generally tubular-shaped prosthetic heart valve 200. The leaflet frame 130f comprises a plurality of spaced apart frame elements 139 defining substantially an isosceles triangles interconnected by a base element 138f defining leaflet windows 137f having the shape of and isosceles trapezoid. Each leaflet window side 133 is defined by a side of one triangle and a side of an adjacent triangle, and wherein each leaflet window base 134 is defined by the base element 138. The term "frame element" as used herein refers to any portion of the leaflet frame 130, such as, but not limited to, those individual portions that define a leaflet window 137.

Referring again to FIGS. 11A and 8D, the leaflet frame first end 131a further comprises commissure posts 136 extending from an apex of the leaflet frame elements defining substantially an isosceles triangle. The commissure post 136 may affect the leaflet free edge 142 so as to create a larger or wider coaptation region 146 between adjacent leaflet free edges 142.

Outer Frame

The outer frame 120 is a generally tubular member defining a generally open pattern of apertures 122, in accordance with an embodiment, as shown in FIG. 1C. The outer frame 120 is comprised of a generally cylindrical arrangement of three triangular-shaped leaflet windows 137, the centers of which are each spaced apart by 120°, as shown in FIG. 2B.

In accordance with transcatheter embodiments, the outer frame 120 is operable to allow it to be compressed and expanded between different diameters. The outer frame 120 comprises an outer frame outer surface 126a and an outer frame inner surface 126b opposite the outer frame outer surface 126a, as shown in FIG. 5A. The outer frame 120 may comprise a structure known in the art as a stent. A stent is a tubular member that may have a small diameter suitable for percutaneous transcatheter delivery into the anatomy, and may be expanded to a larger diameter when deployed into the anatomy. Stents having various designs and material properties are well known in the art.

Figure 1D:
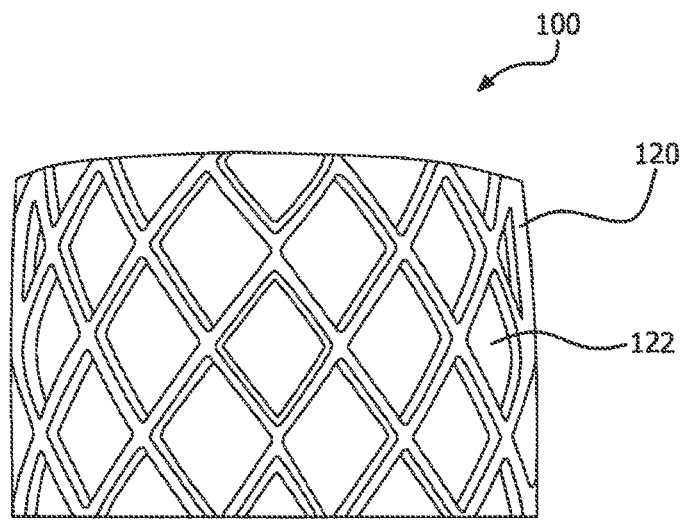
FIG. 1D is a representation of a prosthetic heart valve in an expanded configuration.

By way of example, and as illustrated in the embodiments of FIGS. 1A-1C and 2A-2B, the prosthetic heart valve 100 includes the outer frame 120 that defines a stent having apertures 122 having generally a diamond shape when in a large diameter configuration, as shown generally in FIG. 1D. Upon compression to a smaller diameter, the apertures 122 deform to generally define an elongated diamond shape, as shown generally in FIG. 1E. Upon re-expansion to a larger diameter, the apertures 122 re-expand to again define a generally diamond shape.

As shown in FIGS. 5A and 5B, both views showing the elements in cross-section, the leaflet frame 130 has a generally tubular shape defining a plurality of leaflet windows (not shown). The outer frame 120 has a generally tubular shape. The leaflet frame 130 is coaxially disposed at least partially within the outer frame 120. The leaflet frame 130 and outer frame 120 are coupled at least in part by a contiguous portion of the film 160. At least a portion of the contiguous portion of the film 160 is contained between and couples the leaflet frame 130 to the outer frame 120 to inhibit relative movement therebetween. The film defines a leaflet 140 extending from each of the leaflet windows. The leaflet base 143 is defined at a fold line 145 in the film 160. In accordance with an embodiment, at least a portion of the contiguous portion of the film 160 that is contained between and coupling the leaflet frame 130 and outer frame 120 prevents contact between the leaflet frame 130 and outer frame 120.

Figure 6A:
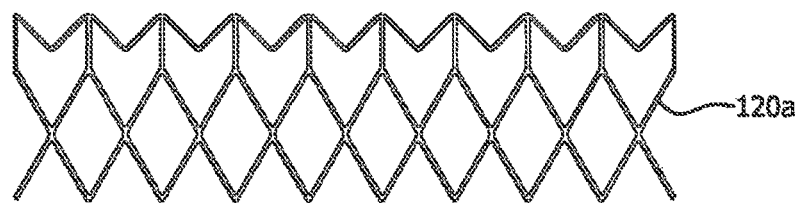
FIG. 6A is an embodiment of an outer frame unrolled to a flat orientation.
Figure 6B:
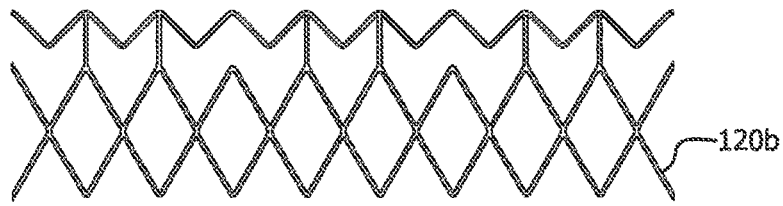
FIG. 6B is an embodiment of an outer frame unrolled to a flat orientation.

FIGS. 6A and 6B are side views of alternative embodiments of the outer frame 120a, 120b wherein the outer frame has been longitudinally cut and laid open to better illustrate the elements of the outer frame An open framework of the stent can define any number of features, repeatable or otherwise, such as geometric shapes and/or linear or meandering series of sinusoids. Geometric shapes can comprise any shape that facilitates substantially uniform circumferential compression and expansion. The outer frame 120 may comprise a cut tube, or any other element suitable for the particular purpose. The outer frame 120 may be etched, cut, laser cut, or stamped into a tube or a sheet of material, with the sheet then formed into a substantially cylindrical structure. Alternatively, an elongated material, such as a wire, bendable strip, or a series thereof, can be bent or braided and formed into a substantially cylindrical structure wherein the walls of the cylinder comprise an open framework that is compressible to a smaller diameter in a generally uniform and circumferential manner and expandable to a larger diameter.

It is known that stents of various designs may be elastically deformable so as to be self-expanding under spring loads. It is also known that stents of various designs may be plastically deformable so as to be mechanically expanded such as with a balloon. It is also known that stents of various designs may be plastically deformable as well as elastically deformable. The embodiments of the outer frame 120 presented herein are not to be limited to a specific stent design or mode of expansion.

The outer frame 120 can comprise any metallic or polymeric biocompatible material. For example, the outer frame 120 can comprise a material, such as, but not limited to nitinol, cobalt-nickel alloy, stainless steel, or polypropylene, acetyl homopolymer, acetyl copolymer, ePTFE, other alloys or polymers, or any other biocompatible material having adequate physical and mechanical properties to function as described herein.

Figure 4A:
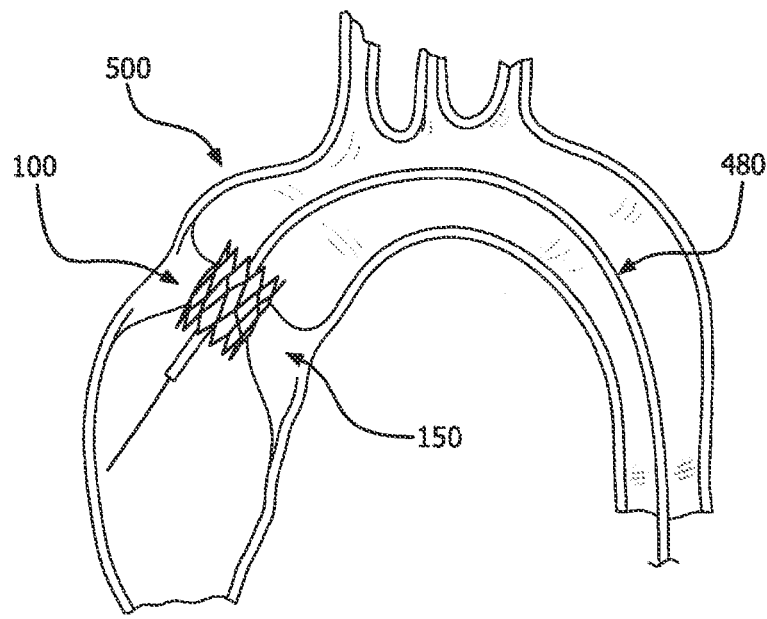
FIG. 4A is a side view of an embodiment of a transcatheter delivery system within anatomy.
Figure 4B:
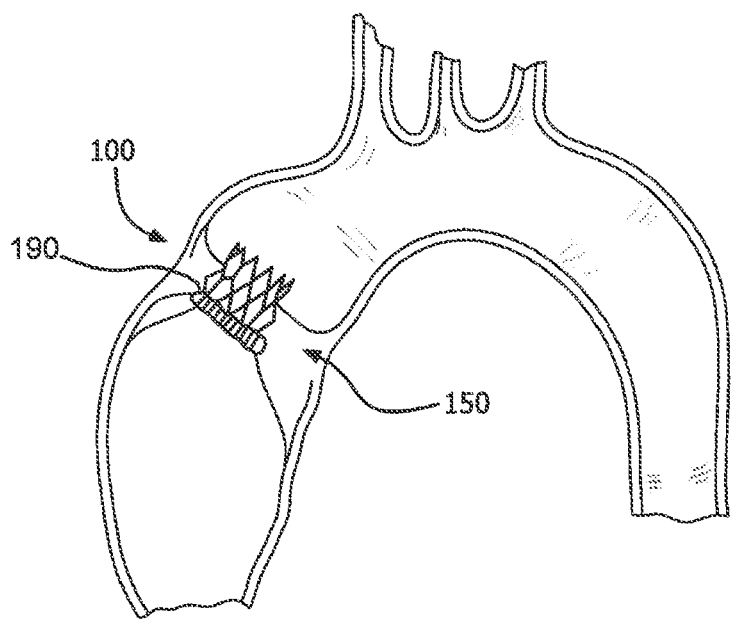
FIG. 4B is a side view of an embodiment of a surgical prosthetic heart valve within anatomy.

In accordance with embodiments, the outer frame 120 and/or leaflet frame 130 can be configured to provide positive engagement with an implant site to firmly anchor the prosthetic heart valve 100 to the site, as shown in FIG. 4A representing a transcatheter deployment of the prosthetic heart valve 100. In accordance with an embodiment, the outer frame 120 can comprise a sufficiently rigid frame having small elastic recoil so as to maintain sufficient apposition against a tissue orifice 150 to maintain position. In accordance with another embodiment, the outer frame 120 and/or leaflet frame 130 can be configured to expand to a diameter that is larger than a tissue orifice 150 so that when prosthetic heart valve 100 expands into the tissue orifice 150, it can be firmly seated therein. In accordance with another embodiment, the outer frame 120 can comprise one or more anchors (not shown) configured to engage the implant site, such as a tissue orifice 150, to secure the prosthetic heart valve 100 to the implant site.

It is appreciated that other elements or means for coupling the prosthetic heart valve 100 to an implant site are anticipated. By way of example, but not limited thereto, other means, such as mechanical and adhesive means may be used to couple the prosthetic heart valve 100 to a synthetic or biological conduit.

Sewing Cuff

In accordance with a surgical valve 100 embodiment, the valve 100 further comprises a sewing cuff 170 about a body frame outer surface 127 in accordance with an embodiment, as shown in FIG. 4B. The sewing cuff 170 is operable to provide structure that receives suture for coupling to the implant site. The sewing cuff 170 may comprise any suitable material, such as, but not limited to, double velour polyester. The sewing cuff 170 may be located circumferentially around a perimeter of the base frame 120. Sewing cuffs are known in the art.

Leaflet Frame

Referring again to FIGS. 1C and 2B, the leaflet frame 130 is a generally tubular member defining a plurality of leaflet windows 137 coupled together by connecting elements 139, in accordance with an embodiment. The leaflet frame 130 comprises a leaflet frame first end 138a and a leaflet frame second end 138b opposite the leaflet frame first end 138a. The leaflet frame 130 comprises a leaflet frame outer surface 132a and a leaflet frame inner surface 132b opposite the outer surface 132a, as shown in FIG. 5A. The leaflet frame first end 138a and the leaflet frame second end 138b define a generally zigzag configuration to facilitate flexion about flex points 136 such as which facilitates compression and expansion between different diameters for compression onto a delivery device and expansion by a balloon for the transcatheter valve 100 embodiments, as generally explained for the outer frame 120. As will be discussed later, the surgical prosthetic heart valve 100 embodiment may or may not have the zigzag configuration since the surgical prosthetic heart valve 100 may be of a fixed diameter and need not be operable to compress and re-expand.

The leaflet frame 130 may be referred to in a general sense as a stent or a frame.

The leaflet frame 130 defines a predetermined repeating pattern as shown in FIG. 2B, in accordance with an embodiment. The leaflet frame 130 defines three interconnected leaflet windows 137 having a substantially triangular shape. Each of the leaflet windows 137 include two leaflet window sides 133, a leaflet window base 134, and a leaflet window top 135. In this embodiment, the leaflet window base 134 defines a flex point 136 which will be described further below. A leaflet window side 133 and leaflet window top 135 of one leaflet window 137 is interconnected with a leaflet window side 133 of an adjacent leaflet window 137.

The leaflet frame 130 defines any number of features and geometric shapes that facilitate substantially uniform circumferential compression and expansion. The leaflet frame 130 may comprise a cut tube, or any other element suitable for the particular purpose. The leaflet frame 130 may be etched, cut, laser cut, or stamped into a tube or a sheet of material, with the sheet then formed into a substantially cylindrical structure. Alternatively, an elongated material, such as a wire, bendable strip, or a series thereof, can be bent or braided and formed into a substantially cylindrical structure wherein the walls of the cylinder comprise an open framework that is compressible to a smaller diameter in a generally uniform and circumferential manner and expandable to a larger diameter.

The leaflet frame 130 can comprise any metallic or polymeric biocompatible material. For example, the leaflet frame 130 can comprise a material, such as, but not limited to nitinol, cobalt-nickel alloy, stainless steel, or polypropylene, acetyl homopolymer, acetyl copolymer, ePTFE, other alloys or polymers, or any other biocompatible material having adequate physical and mechanical properties to function as described herein.

As will be described in more detail below, a film 160 is disposed over each of the three leaflet windows 137 to form a leaflet 140. Further embodiments will be described below wherein the leaflet window 137 defines shapes other than a substantially triangular shape, including, but not limited to a parabolic shape and a trapezoidal shape, with and without a leaflet window top 135, suitable for a particular purpose of an embodiment of a surgical and transcatheter valve 100.

Figure 7A:
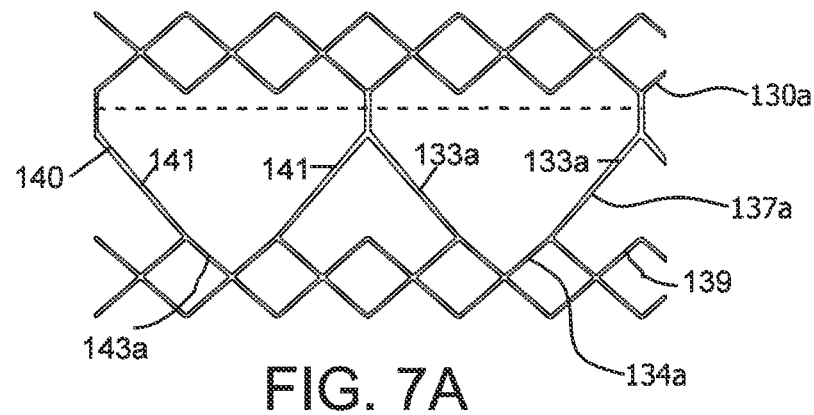
FIG. 7A is an embodiment of a leaflet frame unrolled to a flat orientation.
Figure 7B:
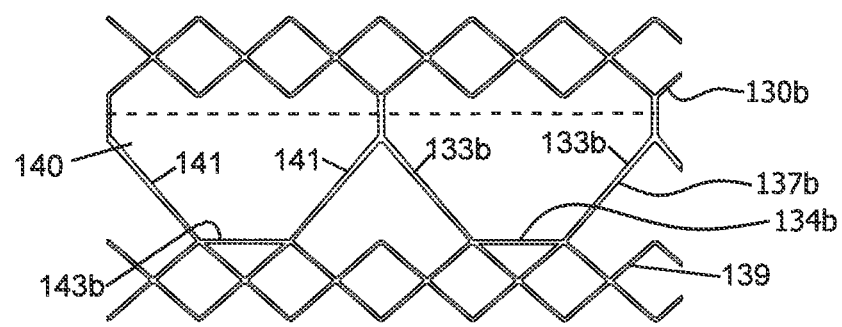
FIG. 7B is an embodiment of a leaflet frame unrolled to a flat orientation.

FIGS. 7A and 7B are side views of alternative embodiments of the leaflet frame 130a, 130b wherein the leaflet frame has been longitudinally cut and laid open to better illustrate the elements of the leaflet frame. The leaflet frame 130a includes leaflet windows 137a having a substantially triangular shape defining a pointed leaflet window base 134a. The leaflet frame 130b includes leaflet windows 137b having a substantially triangular shape defining a flat leaflet window base 134b. The flat leaflet window base 134b may be used to define the leaflet base.

FIGS. 8A-8C are side views of alternative embodiments of the leaflet frame 130c-130e wherein the leaflet frame has been longitudinally cut and laid open to better illustrate the elements of the leaflet frame. The leaflet frame 130c includes leaflet windows 137c having a substantially triangular shape defining a pointed leaflet window base 134c. The leaflet frame 130d includes leaflet windows 137d having a substantially parabolic shape defining a rounded leaflet window base 134d. The flat leaflet window base 134b may be used to define the leaflet base. The leaflet frame 130e includes leaflet windows 137e having a substantially triangular shape defining a pointed leaflet window base 134c but not having a leaflet window top.

FIG. 8d is a side view of an alternative embodiment of the leaflet frame 130f wherein the leaflet frame 130f has been longitudinally cut and laid open to better illustrate the elements of the leaflet frame. The leaflet frame 130f includes leaflet windows 137f having a substantially isosceles trapezoid shape defining a flat leaflet window base 134f. The flat leaflet window base 134f may be used to define the leaflet base. In accordance with other embodiments of the prosthetic valve, each leaflet 140f has substantially the shape of an isosceles trapezoid having two leaflet sides 141f, a leaflet base 142f and a free edge 143f opposite the leaflet base, wherein the two leaflet sides diverge from the leaflet base, wherein the leaflet base is substantially flat, as shown in dashed lines in FIG. 8d.

Figure 8E:
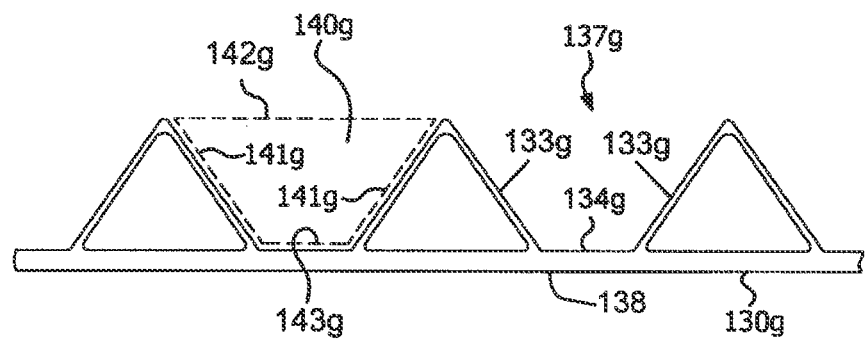
FIG. 8E is an embodiment of a leaflet frame unrolled to a flat orientation.

FIG. 8e is a side view of an alternative embodiment of the leaflet frame 130g wherein the leaflet frame 130g has been longitudinally cut and laid open to better illustrate the elements of the leaflet frame. The leaflet frame 130g includes leaflet windows 137g having a substantially isosceles trapezoid shape defining a flat leaflet window base 134f. The flat leaflet window base 134g may be used to define the leaflet base. In accordance with other embodiments of the prosthetic valve, each leaflet 140g has substantially the shape of an isosceles trapezoid having two leaflet sides 141g, a leaflet base 142g and a free edge 143g opposite the leaflet base, wherein the two leaflet sides diverge from the leaflet base, wherein the leaflet base is substantially flat, as shown in dashed lines in FIG. 8e.

The frame comprises a plurality of spaced apart leaflet windows 137f each leaflet attachment zone defines substantially an isosceles triangle interconnected by a base element 138f, wherein each leaflet window side is defined by a side of one triangle and a side of an adjacent triangle, and wherein each leaflet window base is defined by the base element 138f.

FIG. 7A is a representation of another embodiment of a leaflet frame 130a unrolled to a flat orientation. The leaflet frame 130a comprises frame elements 139 suitable for affecting compression and expansion as would be needed for intravascular placement. The leaflet window 137a is defined by two leaflet window sides 133a that meet at a leaflet window base 134a. A leaflet 140 is shown in dashed line to represent where the leaflet 140 is located within the leaflet window 137a. The leaflet sides 141 are coupled to the leaflet window sides 133a and the leaflet base 143 is coupled to the leaflet window base 134a.

FIG. 7B is a representation of another embodiment of a leaflet frame 130b unrolled to a flat orientation. The leaflet window 137b is defined by two leaflet window sides 133b that meet at a leaflet window base 134b that is elongated and horizontal with the valve axis. A leaflet 140 is shown in dashed line to represent where the leaflet 140 is located within the leaflet window 137a. The leaflet sides 141 are coupled to the leaflet window sides 133a and the leaflet base 143b is coupled to the leaflet window base 134a. The leaflet window base 134b is flat such that the leaflet bends from a flat base during opening and closing.

FIG. 8A is a representation of another embodiment of a leaflet frame 130c unrolled to a flat orientation. The leaflet frame 130c comprises frame elements 139 suitable for affecting compression and expansion as would be needed for intravascular placement. The leaflet window 137c is defined by two leaflet window sides 133c that meet at a leaflet window base 134c. A leaflet 140 is shown in dashed line to represent where the leaflet 140 is located within the leaflet window 137c. The leaflet sides 141 are coupled to the leaflet window sides 133c and the leaflet base 143c is coupled to the leaflet window base 134c.

FIG. 8B is a representation of another embodiment of a leaflet frame 130d unrolled to a flat orientation. The leaflet frame 130d comprises frame elements 139 suitable for affecting compression and expansion as would be needed for intravascular placement. The leaflet window 137d is defined by two leaflet window sides 133d that meet at a leaflet window base 134d. A leaflet 140 is shown in dashed line to represent where the leaflet 140 is located within the leaflet window 137d. The leaflet sides 141 are coupled to the leaflet window sides 133d and the leaflet base 143d is coupled to the leaflet window base 134d. The leaflet window sides 133d define a parabolic shape.

FIG. 8C is a representation of another embodiment of a leaflet frame 130e unrolled to a flat orientation. The leaflet frame 130e comprises frame elements 139 suitable for affecting compression and expansion as would be needed for intravascular placement. The leaflet window 137*e* is defined by two leaflet window sides 133*e* that meet at a leaflet window base 134*e*. A leaflet 140 is shown in dashed line to represent where the leaflet 140 is located within the leaflet window 137*e*. The leaflet sides 141 are coupled to the leaflet window sides 133*e* and the leaflet base 143*e* is coupled to the leaflet window base 134*a*.

FIG. 8D is a side view of an alternative embodiment of the leaflet frame 130*f* wherein the leaflet frame 130*f* has been longitudinally cut and laid open to better illustrate the elements of the leaflet frame 130*f*, of a valve substantially shown as the prosthetic heart valve 100 of FIGS. 11A and 11B. A leaflet 140*f* is shown in dashed line to represent where the leaflet 140*f* is located within the leaflet window 137*f*, the leaflet window 137*f* being defined by the leaflet window sides 133*f* and the leaflet window base 134*f*. The two leaflet sides 141*f* diverge from the leaflet base 143*f*, wherein the leaflet base 143*f* is substantially flat, with the leaflet free edge 142*f* opposite the leaflet base 143*f*, as shown in dashed lines in FIG. 8D. The leaflet frame 130*f* further defines commissure posts 136 from which the leaflet free edge 142*f* extends.

FIG. 8E is a side view of an alternative embodiment of the leaflet frame 130*g* wherein the leaflet frame 130*g* has been longitudinally cut and laid open to better illustrate the elements of the leaflet frame 130*g*. A leaflet 140*g* is shown in dashed line to represent where the leaflet 140*g* is located within the leaflet window 137*g*, the leaflet window 137*g* being defined by the leaflet window sides 133*g* and the leaflet window base 134*g*. Two leaflet sides 141*g* diverge from the leaflet base 143*g*, wherein the leaflet base 143*g* is substantially flat, with the leaflet free edge 142*g* opposite the leaflet base 143*g*, as shown in dashed lines in FIG. 8E. The leaflet frame 130*g* comprises a plurality of leaflet frame elements defining a plurality of isosceles triangles interconnected by a leaflet window base 134*g* defining leaflet windows 137*g* that define isosceles trapezoids. Each leaflet window side 133*g* is defined by a side of one triangle and a side of an adjacent triangle.

Figure 8F:
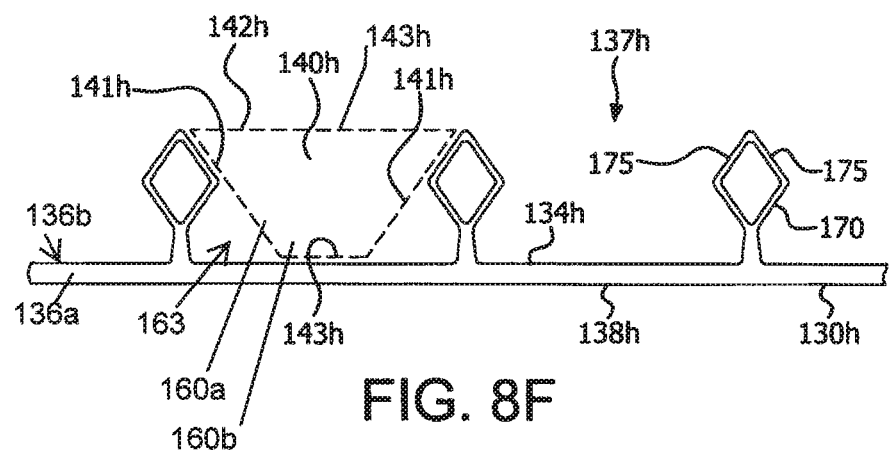
FIG. 8F is an embodiment of a leaflet frame unrolled to a flat orientation.

FIG. 8F is a side view of an alternative embodiment of the leaflet frame 130*h* wherein the leaflet frame 130*h* has been longitudinally cut and laid open to better illustrate the elements of the leaflet frame 130*h*. The leaflet frame 130*h* comprises a base element 138*h* and a plurality of spaced apart spade elements 170 interconnected by the base element 138*h*. Each leaflet window 137*h* is defined by a spade side 175 of one spade element 170 and a spade side 175 of an adjacent spade element 170, and wherein each leaflet window base 134*h* is defined by the base element 138*h*. The spade side 175 does not extend to the base element 138*h*. By virtue of the geometry, the leaflet 140*h*, during opening and closing, will bend about the spade side 175 and towards the base element 138*h* defining a partially frameless leaflet window 137*h* where the leaflet 140 is not bending directly adjacent a frame element 139, defining an attachment zone 163. The leaflet base 143*h* may be defined a distance away from the base element 138*h* such that the leaflet base 143*h* is not bending directly adjacent the base element 138*h*. A leaflet base 143*h* that is not directly adjacent the base element 138*h* is referred herein as a virtual leaflet window base, virtual in the sense that it is not defined directly by a frame element. In accordance with an embodiment of the prosthetic heart valve, each leaflet 140*h* takes the form of substantially the shape of an isosceles trapezoid having two leaflet sides 141*h*, a leaflet base 143*h* and a leaflet free edge 142*h* opposite the leaflet base 143*h*, wherein the two leaflet sides 141*h* diverge from the leaflet base 143*h*, wherein the leaflet base 143*h* is substantially flat, as shown in dashed lines in FIG. 8F.

In accordance with an embodiment, the leaflet frame comprises a frame first end and a frame second end opposite the frame first end, the leaflet window having a shape determined, at least in part, by wrapping a two dimensional isosceles trapezoid onto the tubular shape of the frame, the isosceles trapezoid having a base and two sides that diverge from the base, and wherein a side from adjacent isosceles trapezoids meet at the frame second end.

In another embodiment substantially as shown in FIG. 8F, a first layer of film 160*a* is coupled to a leaflet frame inner surface 132*b* of the leaflet frame 130*h* and a second layer of film 160*b* is coupled to a leaflet frame outer surface 132*a* of the leaflet frame 130*h* opposite from the leaflet frame inner surface 132*b*. The first layer of film 160 and the second layer of film 160*b* are coupled together to define an attachment zone 163.

As previously discussed, the leaflet window base may be used to define the leaflet base in accordance with embodiments. Also as previously discussed, the leaflet base may be defined as a virtual leaflet base 143 by a fold line 145 in the film 160 in the fold region spaced apart from the leaflet window base 134, as shown in FIGS. 1A and 1B, and shown by the dashed lines in FIG. 2B. It is appreciated that there are many embodiments of the outer frame having configurations suitable for the particular purpose.

Figure 10A:
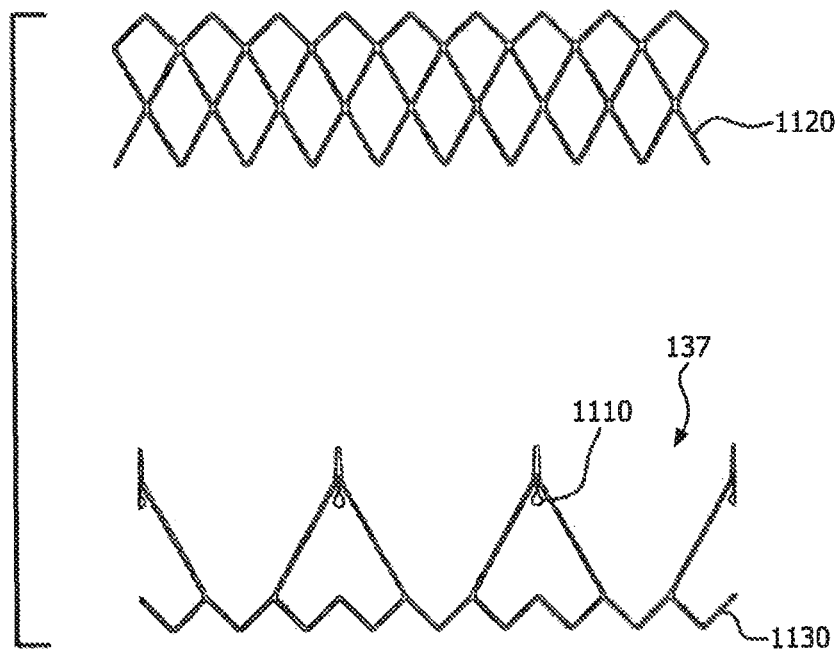
FIG. 10A is a side exploded view of a leaflet frame and an outer frame that may be coupled by a mechanical engagement member, in accordance with another embodiment.
Figure 10B:
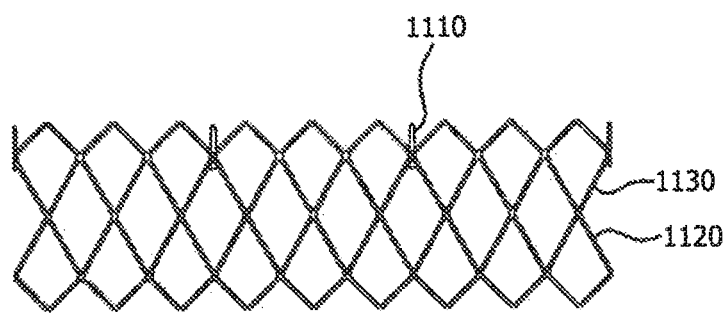
FIG. 10B is a side view of an assembled embodiment of FIG. 10A.

FIG. 10A is a side exploded view of another prosthetic heart valve comprising a leaflet frame 1130 having a generally tubular shape and an outer frame 1120 having a generally tubular shape that are coupled by a mechanical engagement member 1110, in accordance with another embodiment. FIG. 10B is an assembled view of the embodiment of FIG. 10A.

As previously discussed, the leaflet window base may be used to define the leaflet base in accordance with embodiments. Also as previously discussed, the leaflet base may be defined as a virtual leaflet base 143*a* by a fold line 145 in the film 160 in the fold region 144 spaced apart from the leaflet window base, as shown in FIGS. 1B and 2B. It is appreciated that there are many embodiments of the leaflet frame having configurations suitable for the particular purpose.

In transcatheter prosthetic heart valve 100 embodiments, the leaflet frame 130 is elastically, plastically, or both, compressible to obtain a relatively small diameter to accommodate percutaneous transcatheter mounting and delivery.

The leaflet frame 130 may comprise, such as, but not limited to, any elastically deformable metallic or polymeric biocompatible material, in accordance with embodiments. The leaflet frame 130 may comprise a shape-memory material, such as nitinol, a nickel-titanium alloy. Other materials suitable for the leaflet frame 130 include, but are not limited to, other titanium alloys, stainless steel, cobalt-nickel alloy, polypropylene, acetyl homopolymer, acetyl copolymer, other alloys or polymers, or any other biocompatible material having adequate physical and mechanical properties to function as a leaflet frame 130 as described herein.

In accordance with an embodiment, the leaflet frame 130 and the outer frame 120 comprise a shape memory material operable to flex under load and retain its original shape when the load is removed, thus allowing the leaflet frame 130 and the outer frame 120 to self-expand from a compressed shape to a predetermined shape. The leaflet frame 130 and the outer frame 120 may comprise the same or different materials. In accordance with an embodiment the leaflet frame 130 is plastically deformable to be expanded by a balloon.

In another embodiment, the outer frame 120 is elastically deformable so as to be self-expanding.

Film

The film 160 is generally any sheet-like material that is biologically compatible and configured to couple to leaflets to the leaflet frame, in accordance with embodiments. It is understood that the term "film" is used generically for one or more biocompatible materials suitable for a particular purpose. The leaflets 140 are also comprised of the film 160.

In accordance with an embodiment, the film 160 that is not of a biological source and that is sufficiently flexible and strong for the particular purpose, such as a biocompatible polymer. In an embodiment, the film 160 comprises a biocompatible polymer that is combined with an elastomer, referred to as a composite.

It is also understood that the film 160 that is coupled to the outer frame 120 may not be the same film 160 that is coupled to the leaflet frame 130, in accordance with embodiments. Details of various types of film 160 are discussed below. In an embodiment, the film 160 may be formed from a generally tubular material to at least partially cover the outer frame 120 and the leaflet frame 130. The film 160 can comprise one or more of a membrane, composite material, or laminate. Details of various types of film 160 are discussed below.

Leaflet

Each leaflet window 137 is provided with a film 160, which is coupled to a portion of the leaflet window sides 133 with the film 160 defining a leaflet 140. Each leaflet 140 defines a leaflet free edge 142 and a leaflet base 143, in accordance with an embodiment. As will be described below, it is anticipated that a plurality of embodiments of leaflet base configurations may be provided. In accordance with an embodiment, the film 160 is coupled to a portion of the leaflet window sides 133 and to the leaflet window base 134 where the leaflet 140 is defined by the portion of the leaflet window sides 133 and to the leaflet window base 134. In accordance with another embodiment, the film 160 is coupled to a portion of the leaflet window sides 133 but not the leaflet window base 134 of the leaflet frame 130 where the leaflet 140 is defined by the portion of the leaflet window sides 133 and to a virtual leaflet base 1033 defined in a fold region as will be described below.

The shape of the leaflets 140 are defined in part by the shape of the leaflet window 137 and the leaflet free edge 142. As will be discussed below in accordance with an embodiment, the shape of the leaflets 140 also depends in part on a process that induces a fold at the fold line 145 to define a virtual leaflet base 143a as will be described further below, so as to impart a predetermined shape to the leaflet 140. Since high bending stresses are located at the leaflet base, defining a virtual leaflet base 143a that is not bound by the leaflet window base 134 may reduce the chance of tearing of the leaflet 140 at the leaflet base 143-leaflet window base 134 interface. It may also reduce blood pooling and stagnation at the leaflet base as compared with a rounded leaflet base.

When the leaflets 140 are in a fully open position, the prosthetic heart valve 100 presents a substantially circular valve orifice 102 as shown in FIG. 3A. Fluid flow is permitted through the valve orifice 102 when the leaflets 140 are in an open position.

As the leaflets 140 cycle between the open and closed positions, the leaflets 140 generally flex about the leaflet base 143 and the portion of the leaflet window sides 133 to which the leaflet are coupled. When the prosthetic heart valve 100 is closed, generally about half of each leaflet free edge 142 abuts an adjacent half of a leaflet free edge 142 of an adjacent leaflet 140, as shown in FIG. 3B. The three leaflets 140 of the embodiment of FIG. 3B meet at a triple point 148. The valve orifice 102 is occluded when the leaflets 140 are in the closed position stopping fluid flow.

Referring to FIG. 3B, in accordance with an embodiment, each leaflet 140 includes a central region 182 and two side regions 184 on opposite sides of the central region 182. The central region 182 is defined by a shape substantially that of an isosceles triangle defined by two central region sides 183, the leaflet base 143 and the leaflet free edge 142. The two central region sides 183 converge from the leaflet base 143 to the leaflet free edge 142. Each of the side regions 184 have a shape substantially that of a triangle and each are defined by one of the central region sides 183, one of the leaflet sides 141, and the leaflet free edge 142.

In accordance with an embodiment, each of the two side regions 184 and the central region 182 are substantially planar when the prosthetic heart valve 100 is in the closed position.

The leaflet 140 can be configured to actuate at a pressure differential in the blood caused, for example, by the contraction of a ventricle or atrium of the heart, such pressure differential typically resulting from a fluid pressure building up on one side of the prosthetic heart valve 100 when closed. As the pressure on an inflow side of the prosthetic heart valve 100 rises above the pressure on the outflow side of the prosthetic heart valve 100, the leaflet 140 opens and blood flows therethrough. As blood flows through the prosthetic heart valve 100 into a neighboring chamber or blood vessel, the pressure equalizes. As the pressure on the outflow side of the prosthetic heart valve 100 rises above the blood pressure on the inflow side of the prosthetic heart valve 100, the leaflet 140 returns to the closed position generally preventing the retrograde flow of blood through the inflow side of the prosthetic heart valve 100.

It is understood that the leaflet frame 130 may comprise any number of leaflet windows 137, and thus leaflets 140, suitable for a particular purpose, in accordance with embodiments. Leaflet frames 130 comprising one, two, three or more leaflet windows 137 and corresponding leaflets 140 are anticipated.

Figure 1E:
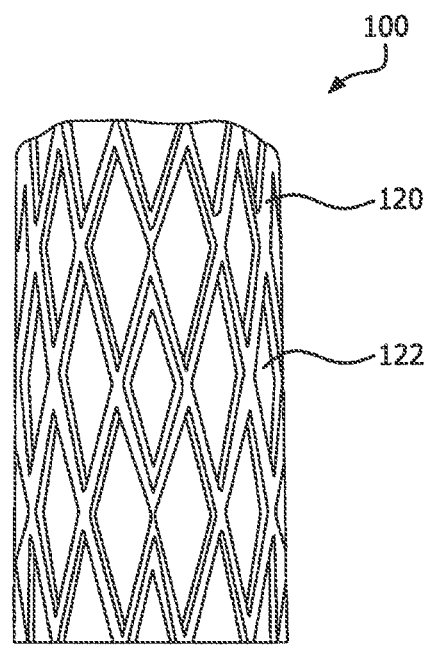
FIG. 1E is a representation of a prosthetic heart valve in a compressed configuration.

In accordance with an embodiment of a transcatheter prosthetic heart valve 100, with reference to FIGS. 1D-1E, the prosthetic heart valve 100 may be compressed into a collapsed configuration having a smaller diameter and expanded into an expanded configuration so that the prosthetic heart valve 100 can be delivered via catheter in the collapsed configuration and expanded upon deployment within the tissue orifice 150 as shown in FIG. 4A. The outer frame 120 can be operable to recover circumferential uniformity when transitioning from the collapsed configuration to the expanded configuration.

Leaflet Film

The film 160 that makes up the leaflet 140 can comprise any biological tissue or synthetic, biocompatible materials sufficiently compliant and flexible, such as a biocompatible polymer. In an embodiment, the leaflet 140 comprises a biocompatible polymer that is combined with an elastomer, referred to as a composite. A material according to one embodiment includes a composite material comprising an expanded fluoropolymer membrane, which comprises a plurality of spaces within a matrix of fibrils, and an elastomeric material. It should be appreciated that multiple types of fluoropolymer membranes and multiple types of elastomeric materials can be combined to form a laminate while remaining within the scope of the present disclosure. It should also be appreciated that the elastomeric material can include multiple elastomers, multiple types of non-elastomeric components, such as inorganic fillers, therapeutic agents, radiopaque markers, and the like while remaining within the scope of the present disclosure.

In accordance with an embodiment, the composite material includes an expanded fluoropolymer material made from porous ePTFE membrane, for instance as generally described in U.S. Pat. No. 7,306,729 to Bacino.

The expandable fluoropolymer, used to form the expanded fluoropolymer material described, may comprise PTFE homopolymer. In alternative embodiments, blends of PTFE, expandable modified PTFE and/or expanded copolymers of PTFE may be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

The expanded fluoropolymer membrane can comprise any suitable microstructure for achieving the desired leaflet performance. In accordance with an embodiment, the expanded fluoropolymer comprises a microstructure of nodes interconnected by fibrils, such as described in U.S. Pat. No. 3,953,566 to Gore. The fibrils radially extend from the nodes in a plurality of directions, and the membrane has a generally homogeneous structure. Membranes having this microstructure may typically exhibit a ratio of matrix tensile strength in two orthogonal directions of less than 2, and possibly less than 1.5.

In another embodiment, the expanded fluoropolymer membrane has a microstructure of substantially only fibrils, as is generally taught by U.S. Pat. No. 7,306,729, to Bacino. The expanded fluoropolymer membrane having substantially only fibrils, can possess a high surface area, such as greater than 20 m$^2$/g, or greater than 25 m$^2$/g, and in some embodiments can provide a highly balanced strength material having a product of matrix tensile strengths in two orthogonal directions of at least 1.5×10$^5$ MPa$^2$, and/or a ratio of matrix tensile strengths in two orthogonal directions of less than 4, and possibly less than 1.5.

The expanded fluoropolymer membrane can be tailored to have any suitable thickness and mass to achieve the desired leaflet performance. By way of example, but not limited thereto, the leaflet 140 comprises an expanded fluoropolymer membrane having a thickness of about 0.1 μm. The expanded fluoropolymer membrane can possess a mass per area of about 1.15 g/m$^2$. Membranes according to an embodiment of the invention can have matrix tensile strengths of about 411 MPa in the longitudinal direction and 315 MPa in the transverse direction.

Additional materials may be incorporated into the pores or within the material of the membranes or in between layers of membranes to enhance desired properties of the leaflet. Composite materials described herein can be tailored to have any suitable thickness and mass to achieve the desired leaflet performance. Composite materials according to embodiments can include fluoropolymer membranes and have a thickness of about 1.9 μm and a mass per area of about 4.1 g/m$^2$.

The expanded fluoropolymer membrane combined with elastomer to form a composite material provides the elements of the present disclosure with the performance attributes required for use in high-cycle flexural implant applications, such as prosthetic heart valve leaflets, in various ways. For example, the addition of the elastomer can improve the fatigue performance of the leaflet by eliminating or reducing the stiffening observed with ePTFE-only materials. In addition, it may reduce the likelihood that the material will undergo permanent set deformation, such as wrinkling or creasing, that could result in compromised performance. In one embodiment, the elastomer occupies substantially all of the pore volume or space within the porous structure of the expanded fluoropolymer membrane. In another embodiment the elastomer is present in substantially all of the pores of the at least one fluoropolymer layer. Having elastomer filling the pore volume or present in substantially all of the pores reduces the space in which foreign materials can be undesirably incorporated into the composite. An example of such foreign material is calcium that may be drawn into the membrane from contact with the blood. If calcium becomes incorporated into the composite material, as used in a prosthetic heart valve leaflet, for example, mechanical damage can occur during cycling open and closed, thus leading to the formation of holes in the leaflet and degradation in hemodynamics.

In an embodiment, the elastomer that is combined with the ePTFE is a thermoplastic copolymer of tetrafluoroethylene (TFE) and perfluoromethyl vinyl ether (PMVE), such as described in U.S. Pat. No. 7,462,675 to Chang et al. As discussed above, the elastomer is combined with the expanded fluoropolymer membrane such that the elastomer occupies substantially all of the void space or pores within the expanded fluoropolymer membrane to form a composite material. This filling of the pores of the expanded fluoropolymer membrane with elastomer can be performed by a variety of methods. In one embodiment, a method of filling the pores of the expanded fluoropolymer membrane includes the steps of dissolving the elastomer in a solvent suitable to create a solution with a viscosity and surface tension that is appropriate to partially or fully flow into the pores of the expanded fluoropolymer membrane and allow the solvent to evaporate, leaving the filler behind.

In one embodiment, the composite material comprises three layers: two outer layers of ePTFE and an inner layer of a fluoroelastomer disposed therebetween. Additional fluoroelastomers can be suitable and are described in U.S. Publication No. 2004/0024448 to Chang.

In another embodiment, a method of filling the pores of the expanded fluoropolymer membrane includes the steps of delivering the filler via a dispersion to partially or fully fill the pores of the expanded fluoropolymer membrane.

In another embodiment, a method of filling the pores of the expanded fluoropolymer membrane includes the steps of bringing the porous expanded fluoropolymer membrane into contact with a sheet of the elastomer under conditions of heat and/or pressure that allow elastomer to flow into the pores of the expanded fluoropolymer membrane.

In another embodiment, a method of filling the pores of the expanded fluoropolymer membrane includes the steps of polymerizing the elastomer within the pores of the expanded fluoropolymer membrane by first filling the pores with a prepolymer of the elastomer and then at least partially curing the elastomer.

After reaching a minimum percent by weight of elastomer, the leaflets constructed from fluoropolymer materials or ePTFE generally performed better with increasing percentages of elastomer resulting in significantly increased cycle lives. In one embodiment, the elastomer combined with the ePTFE is a thermoplastic copolymer of tetrafluoroethylene and perfluoromethyl vinyl ether, such as described in U.S. Pat. No. 7,462,675 to Chang et al., and other references that would be known to those of skill in the art. Other biocompatible polymers which can be suitable for use in leaflet 140 include but are not limited to the groups of urethanes, silicones(organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

Other Considerations

In accordance with an embodiment, the prosthetic heart valve can be configured to prevent interference with a heart conduction system by not covering a bundle branch in the left ventricle when implanted, such as might be encountered with an aortic valve replacement procedure. For example, the prosthetic heart valve can comprise a length of less than about 25 mm or less than about 18 mm. The prosthetic heart valve can also comprise an aspect ratio of less than one, wherein the ratio describes the relationship between the length of the prosthetic heart valve to the expanded, functional diameter. However, the prosthetic heart valve can be constructed at any length and, more generally, any desirable dimension.

In a transcatheter embodiment, in a collapsed state, the prosthetic heart valve can have a collapsed profile that is less than about 35% of the expanded profile. For example, the prosthetic heart valve 100 comprising a 26 mm expanded diameter can have a collapsed diameter of less than about 8 mm, or less than about 6 mm. The percent difference in diameter is dependent on dimensions and materials of the prosthetic heart valve and its various applications, and therefore, the actual percent difference is not limited by this disclosure.

The prosthetic heart valve can further comprise a bioactive agent. Bio-active agents can be coated onto a portion or the entirety of the film 160 for controlled release of the agents once the prosthetic heart valve is implanted. The bio-active agents can include, but are not limited to, vasodilator, anti-coagulants, anti-platelet, anti-thrombogenic agents such as, but not limited to, heparin. Other bio-active agents can also include, but are not limited to agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

Transcatheter Delivery System

In an embodiment, with reference to FIG. 4A, a valve delivery system 500 comprises a prosthetic heart valve 100 having a collapsed configuration and an expanded configuration as previously described and an elongated flexible catheter 480, such as a balloon catheter, configured to deploy the prosthetic heart valve 100 via catheter. The catheter 480 can comprise a balloon to expand the prosthetic heart valve 100 and/or if required, to touch up the prosthetic heart valve 100 to ensure proper seating. The prosthetic heart valve 100 can be mounted to the distal section of the catheter 480 for delivery through the vasculature. In order to hold the prosthetic heart valve in a collapsed configuration on the catheter 480, the valve delivery system may further comprise a removable sheath (not shown) to closely fit over the transcatheter prosthetic heart valve 100.

A method of delivery can comprise the steps of radially compressing a prosthetic heart valve into its collapsed configuration onto the distal end of an elongate flexible catheter having proximal and distal ends; delivering the prosthetic heart valve to a tissue orifice, such as a native aortic valve orifice, via a transfemoral or transapical route, and expanding the prosthetic heart valve into the tissue orifice. The prosthetic heart valve can be expanded by inflating a balloon.

A method of delivery can comprise the steps of radially compressing a prosthetic heart valve into its collapsed configuration, onto the distal section of an elongated flexible catheter having proximal and distal ends. A restraint, which can be connected to a tether that passes through the orifice of the prosthetic heart valve and the lumen of the catheter, is fitted around the commissure posts of the prosthetic heart valve. The prosthetic heart valve is then delivered to a native valve orifice, such as a native aortic valve orifice, via a route of delivery and expanded into the native orifice. The route of delivery can comprise a transfemoral or transapical route. The prosthetic heart valve can be expanded by inflating a balloon.

Surgical Embodiments

It is appreciated that the embodiments of the prosthetic heart valve 100 may be surgically implanted rather than using transcatheter techniques. Embodiments of a surgically implanted prosthetic heart valve 100 may be substantially the same as those described above, with the addition of a sewing cuff 190 adjacent to the outer frame outer surface 126a, shown in FIG. 4B, in accordance with an embodiment. The sewing cuff 190, which is well known in the art, is operable to provide structure that receives suture for coupling the prosthetic heart valve 100 to an implant site, such as the tissue orifice 150. The sewing cuff 190 may comprise any suitable material, such as, but not limited to, double velour polyester. The sewing cuff 190 may be located circumferentially around the outer frame 120.

Method of Making

Figure 9A:
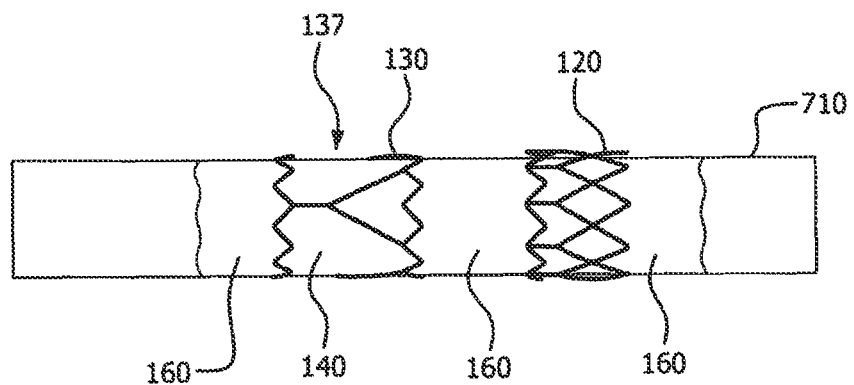
FIG. 9A is a side view of a leaflet frame and an outer frame on an assembly mandrel, in accordance with an embodiment.

Embodiments described herein also pertain to a method of making the prosthetic heart valve 100 embodiments as described herein. In order to make the various embodiments, a cylindrical mandrel 710 can be used. With reference to FIG. 9A, the mandrel 710 comprises a structural form operable to receive the outer frame 120 thereon.

Figure 9B:
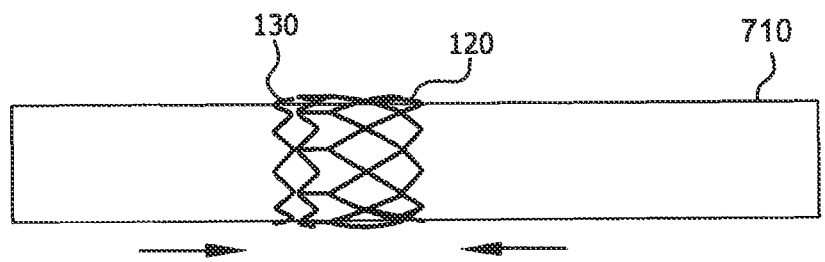
FIG. 9B is a side view of the leaflet frame and the outer frame as nested together on an assembly mandrel, in accordance with the embodiment of FIG. 9A.

With reference to FIGS. 9A and 9B, an embodiment of a method of making a prosthetic heart valve 100 comprises the steps of wrapping a first layer of film 160, e.g., a composite as described herein, into a tubular form about the mandrel 710; placing the leaflet frame 130 and outer frame 120 over the first layer of film 160, as shown in FIG. 9A; forming a second layer of film 160 over the leaflet frame 130 and the outer frame 120; thermally setting the assembly; cutting the film 160 across the leaflet window top within the leaflet window 137, masking with release material 170 a portion of the film 160 in the leaflet window that defines the leaflet 140 to prevent further bonding of leaflet 140 during subsequent processing steps; wrapping a second layer of film 160 into a tubular form over the 120, and over the first layer of film 160; thermal setting the assembly; remove the assembly from the mandrel.

Figure 12:
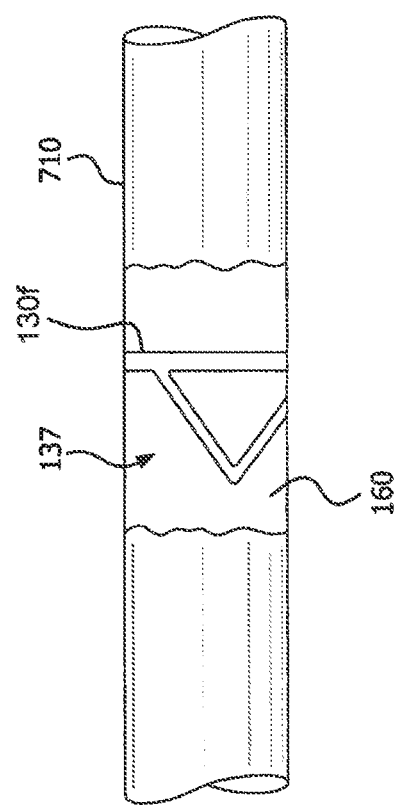
FIG. 12 is a side view of a leaflet frame on an assembly mandrel, in accordance with an embodiment of FIGS. 11A and 11B.
Figures 13A, 13B:
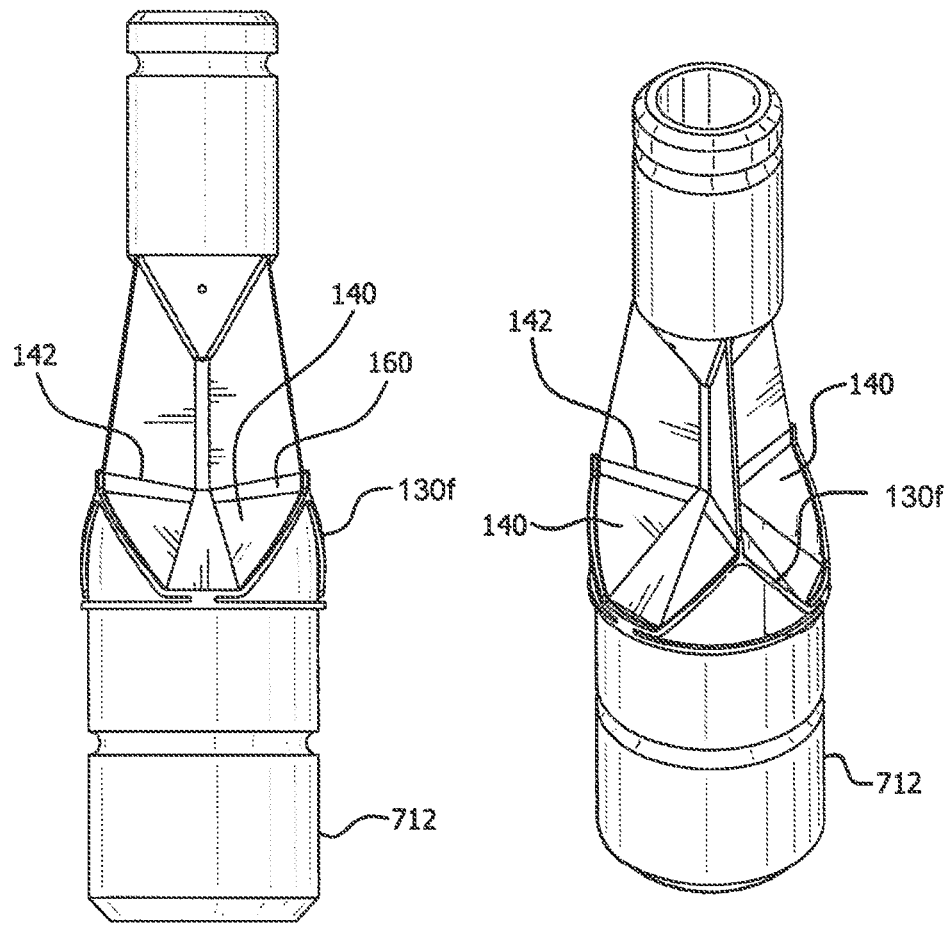
FIG. 13A is a side view of the leaflet frame on a cutting mandrel, in accordance with an embodiment.
FIG. 13B is a perspective view of the leaflet frame on the cutting mandrel of FIG. 13A.
Figure 14:
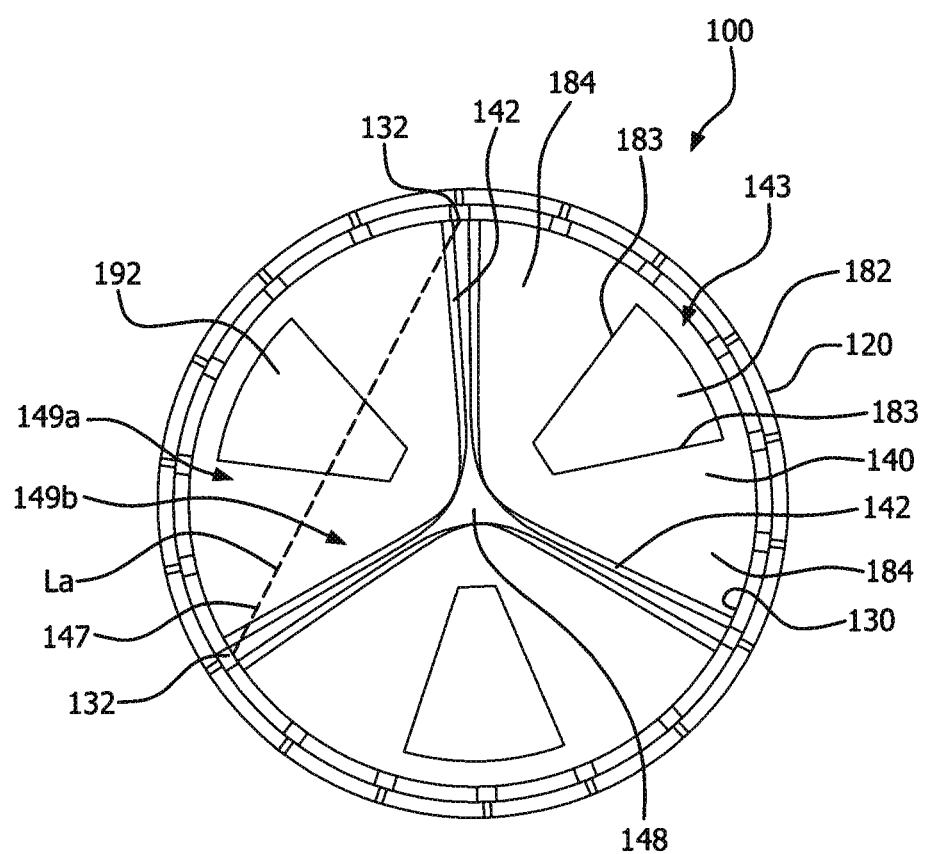
FIG. 14 is an axial view of an embodiment of a prosthetic heart valve in an open configuration.
Figure 15:
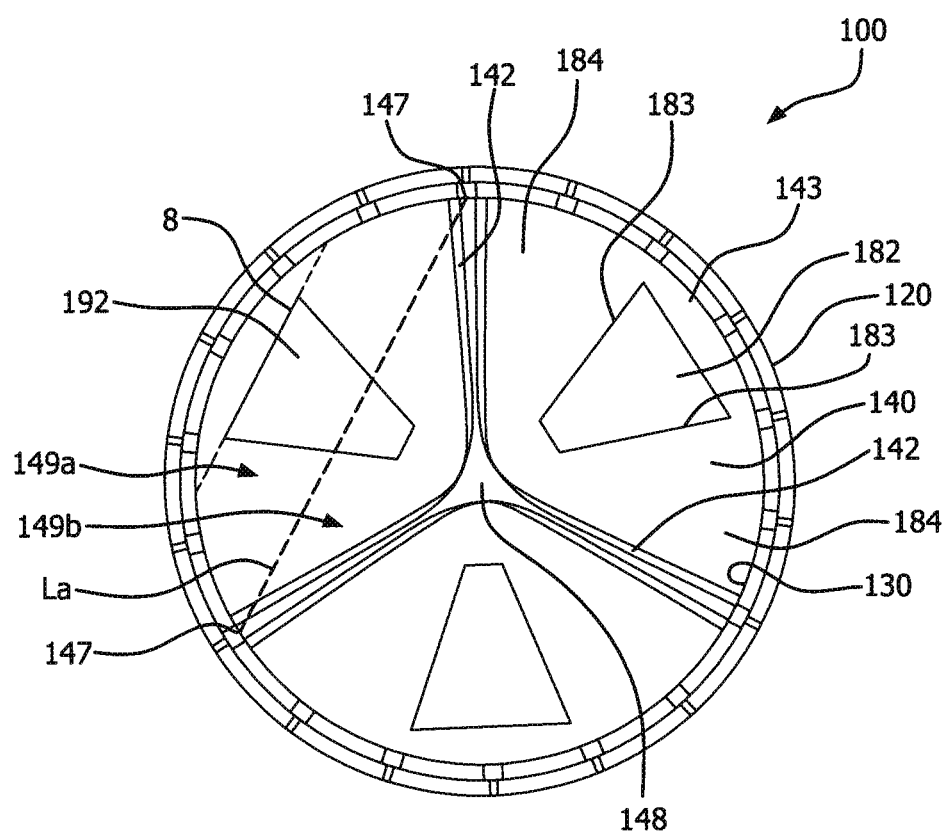
FIG. 15 is an axial view of an embodiment of a prosthetic heart valve in an open configuration.

Embodiments described herein also pertain to a method of making the prosthetic heart valve 200 embodiments as described herein. In order to make the various embodiments, a cylindrical mandrel 710 can be used. With reference to FIG. 12, the mandrel 710 comprises a structural form operable to receive the leaflet frame 130 thereon. An embodiment of a method of making a prosthetic heart valve 200 comprises the steps of wrapping a first layer of film 160, e.g., a composite as described herein, into a tubular form about the mandrel 710; placing the leaflet frame 130 over the first layer of film 160, as shown in FIG. 12; forming a second layer of film 160 over the leaflet frame 130; thermally setting the assembly; receiving the assembly over a cutting mandrel 712 as shown in FIGS. 13A and 13B; cutting the film 160 across the leaflet window top within the leaflet window 137, resulting in the prosthetic heart valve 200 of FIGS. 11A and 11B. FIG. 11A is a side view of an embodiment of a prosthetic heart valve and FIG. 11B is a perspective view of the embodiment of the prosthetic heart valve of FIG. 11A. In FIGS. 11A and 11B the leaflets 140 are shown slightly open as when held by the cutting mandrel 712. It is understood that a fully closed prosthetic heart valve 200 will have the leaflet free edges 142 of the leaflets 140 coming together to coapt under the influence of downstream fluid pressure which results in closing the valve to prevent downstream blood from flowing retrograde through the valve.

EXAMPLES

Example 1

A prosthetic heart valve was produced having polymeric leaflets formed from a composite material having an expanded fluoropolymer membrane and an elastomeric material and joined between two collapsible metallic frames.

The leaflet frame and outer frame were laser machined from a length of SS316LVM tube hard tempered with an outside diameter of 23.0 mm and a wall thickness of 0.65 mm in the shape shown illustratively and generally indicated in FIG. 9A. The leaflet frame 130 and outer frame 120 were electro-polished resulting in 0.0127 mm material removal from each surface and leaving the edges rounded.

Fluorinated ethylene propylene (FEP) powder (Daikin America, Orangeburg N.Y.) was then applied to the leaflet frame 130 and outer frame 120. More specifically, the FEP powder was stirred to form an airborne "cloud" in an enclosed blending apparatus, such as a standard kitchen type blender, while the leaflet frame and outer frame were suspended in the cloud. The leaflet frame and outer frame were exposed to the FEP powder cloud until a uniform layer of powder was adhered to the entire surface of the leaflet frame and outer frame. The leaflet frame and outer frame were then subjected to a thermal treatment by placing it in a forced air oven set to 320° C. for approximately three minutes. This caused the powder to melt and adhere as a thin coating over the entire leaflet frame and outer frame. The leaflet frame and outer frame were removed from the oven and left to cool to room temperature.

Initial Assembly and Thermal Process Cycle

A 21 mm diameter vented metal cylindrical mandrel having a diameter corresponding to the inner diameter of the leaflet frame 130 and outer frame 120 was helically wrapped with sintered ePTFE fiber. A thin film of type 1 (ASTM D3368) FEP was constructed using melt extrusion and stretching. The type 1 (ASTM D3368) FEP film was about 40 μm thick and was about 7.7 cm wide. The mandrel was helically wrapped with one layer of this type 1 FEP film over the sintered ePTFE fiber only in the region of outer frame.

The mandrel was radially wrapped with five layers of an ePTFE membrane with an FEP coating towards the mandrel. The ePTFE membrane was manufactured according to the general teachings described in U.S. Pat. No. 7,306,729. The ePTFE membrane had a mass per area of 2.3 g/m$^2$, a bubble point of 101.5 MPa, a thickness of about 356 nm, a matrix tensile strength of 319 MPa in the longitudinal direction and 407 MPa in the transverse direction.

The mandrel was helically wrapped with one layer of type 1 FEP film.

The diameter of the leaflet frame and outer frame were expanded slightly and received on the wrapped mandrel with approximately a 10 mm space between them, rotational alignment was not necessary.

The leaflet frame, outer frame and the space therebetween were helically wrapped with 1 layer of type 1 FEP film.

The leaflet frame, outer frame and the space therebetween that will become the bridge portion 162 and the fold region 144, as shown in FIG. 2B, were circumferentially wrapped with 5 layers of the same ePTFE membrane with an FEP coating as described above with the coating toward the mandrel.

The wrapped leaflet frame, outer frame and the space therebetween were wrapped with several layers of an ePTFE membrane imbibed with a polyimide material referred to as a release liner.

A substantially nonporous ePTFE membrane was configured into a cylinder and placed over the assembly, referred to as sacrificial tube. Sintered ePTFE fiber was used to seal both ends of the sacrificial tube against the mandrel.

The assembly, including the mandrel, was heated in an oven capable of applying pneumatic pressure external to the sacrificial tube described above and while maintaining a vacuum internal to the mandrel for 40 min such that the mandrel temperature reached approximately 360° C. The assembly was removed from the oven and allowed to cool to room temperature while still pressurized and under vacuum.

The sacrificial tube and release liner was removed. The sintered ePTFE fiber was removed to release the frame assembly from the mandrel.

The polymeric material was trimmed and removed from the leaflet windows of the leaflet frame. The ends of each leaflet frame and outer frame were circumferentially trimmed by a scalpel.

Intermediate Assembly and Thermal Process Cycle

An unsintered 15 mm diameter ePTFE tube was disposed on a 21.5 mm vented metal mandrel. Two layers of a substantially nonporous ePTFE membrane with a FEP coating was circumferentially wrapped on the mandrel with the coating side towards the mandrel. The wrapped mandrel was placed in a convection oven set to 320° C. and heated for 20 min. The ePTFE and substantially nonporous ePTFE membrane combined to serve as a release liner and was perforated to communicate pressure between the vent holes in the mandrel.

The leaflet frame was disposed onto the vented metal mandrel and vent holes were made in the apertures of the leaflet frame over the mandrel vent holes.

A leaflet material was then prepared. A membrane of ePTFE was manufactured according to the general teachings described in U.S. Pat. No. 7,306,729. The ePTFE membrane had a mass per area of 0.452 g/m$^2$, a thickness of about 508 nm, a matrix tensile strength of 705 MPa in the longitudinal direction and 385 MPa in the transverse direction. This membrane was imbibed with a fluoroelastomer. The copolymer consists essentially of between about 65 and 70 weight percent perfluoromethyl vinyl ether and complementally about 35 and 30 weight percent tetrafluoroethylene.

The fluoroelastomer was dissolved in Novec HFE7500 (3M, St Paul, Minn.) in a 2.5% concentration. The solution was coated using a Mayer bar onto the ePTFE membrane (while being supported by a polypropylene release film) and dried in a convection oven set to 145° C. for 30 seconds. After two coating steps, the final ePTFE/fluoroelastomer or composite had a mass per area of 1.75 g/m$^2$, 29.3% fluoropolymer by weight, a dome burst strength of about 8.6 KPa, and thickness of 0.81 µm.

The following test methods were used to characterize the ePTFE layers and the multi-layered composite. The thickness was measured with a Mutitoyo Snap Gage Absolute, 12.7 mm (0.50") diameter foot, Model ID-C112E, Serial #10299, made in Japan. The density was determined by a weight/volume calculation using an Analytical Balance Mettler PM400 New Jersey, USA. The force to break and tensile strengths were measured using an Instron Model #5500R Norwood, Mass., load cell 50 kg, gage length=25.4 cm, crosshead speed=25 mm/minute (strain rate=100% per minute) with flat faced jaws. Unless otherwise noted, these test methods were used to generate the data in subsequent examples.

Ten layers of the composite leaflet material were wrapped around the leaflet frame with an elastomer rich side of the composite facing towards the mandrel. In exemplary embodiments, the composite material is oriented to have a predetermined matrix tensile strength along a direction generally perpendicular with the longitudinal axis of the combined tool assembly. More specifically, the predetermined matrix tensile strength is about 705 MPa.

The mandrel was radially wrapped with one layer of a substantially nonporous ePTFE membrane with an FEP coating towards the mandrel with a spacing 8 mm from the base of the leaflet frame. The ePTFE membrane was manufactured according to the general teachings described in U.S. Pat. No. 7,306,729. The ePTFE membrane had a mass per area of about 11 g/m$^2$, a thickness of about 5.5 µm, a matrix tensile strength of 310 MPa in the longitudinal direction and 103 MPa in the transverse direction.

A Kapton® (EI DuPont de Nemours, Inc., Wilmington, Del.) polyimide film acting as a mask was wrapped over the substantially nonporous ePTFE membrane with an FEP coating layer.

The outer frame was placed on the mandrel with 10 mm spacing between the leaflet frame and the outer frame. The leaflet frame and the outer frame were aligned such that the longitudinal outer frame posts were collinear with the leaflet frame commissure posts.

The leaflet frame and outer frame were wrapped with 24 layers of the composite leaflet material described earlier with an elastomer rich side of the composite facing towards the mandrel. In exemplary embodiments, the composite material is oriented to have a predetermined matrix tensile strength along a direction generally perpendicular with the longitudinal axis of the combined tool assembly. More specifically, the predetermined matrix tensile strength is about 705 MPa.

The final leaflet was comprised of 29.3% fluoropolymer by weight with a thickness of approximately 27 µm. Each leaflet had 34 layers of the composite and a ratio of thickness/number of layers of 0.8 µm.

The mandrel was again radially wrapped with one layer of a substantially nonporous ePTFE membrane with an FEP coating towards the mandrel with a spacing 8 mm from the base of the leaflet frame.

The assembly was wrapped with several layers of the sacrificial release liner. A sacrificial tube was placed over the assembly and sintered ePTFE fiber was used to seal both ends of the sacrificial tube against the mandrel.

The assembly was processed in an oven capable of applying pneumatic pressure external to the sacrificial material configured into a tube described above and while maintaining a vacuum internal to the tube for 25 min such that the mandrel temperature reached approximately 330° C. The assembly was removed from the oven and allowed to cool to room temperature while still pressurized and under vacuum.

The sacrificial tube and liner were removed from the frame assembly and the frame assembly was removed from the mandrel. The Kapton® mask was removed.

A scalpel was used to circumferentially trim the leaflet free edge of each leaflet and the distal end of leaflet frame.

Final Assembly and Thermal Process Cycle

The outer frame was radially expanded to a 24 mm diameter using a tapered mandrel.

A release liner as described above was placed on a 21.5 mm vented mandrel.

Three Kapton® masks were cut to the shape of leaflet window with a 30 mm tapered extension.

The leaflet frame and outer frame with leaflet material were placed onto the mandrel and the tapered extensions of the Kapton® masks were inserted under the top ring of the leaflet frame from the trimmed end and were advanced axially until the masks aligned with the leaflet window.

The leaflet frame was wrapped with 2 layers of the type 1 FEP film.

A hot iron was used to remove the FEP film from the leaflet window region by melting it away from the perimeter and to tack the FEP film in all regions of leaflet frame outside the masks.

Vent holes were made within all the leaflet frame apertures and in the polymer tube region connecting the inner frame and outer frame.

While holding the leaflet frame in place, the outer frame was coaxially disposed over the leaflet frame by telescopically inverting the bridge portion of the contiguous tube.

The entire frame assembly was circumferentially wrapped with one substantially nonporous ePTFE membrane with an FEP coating towards the mandrel.

The assembly was wrapped with several layers of the sacrificial release liner. A sacrificial tube was placed over the assembly and sintered ePTFE fiber was used to seal both ends of the sacrificial tube against the mandrel.

The assembly was processed in an oven capable of applying pneumatic pressure external to the sacrificial material configured into a tube described above and while maintaining a vacuum internal to the tube for 25 min such that the mandrel temperature reached approximately 330° C. The assembly was removed from the oven and allowed to cool to room temperature while still pressurized and under vacuum.

The frame assembly was removed from the mandrel.

A scalpel was used to circumferentially trim each end of leaflet frame.

The Kapton was rotationally peeled away from inside the outer frame and away from leaflets.

Using scissors, both ends of the leaflet frame were trimmed to follow frame contour.

The resulting prosthetic heart valve 100 includes leaflets 140 formed from a composite material with more than one fluoropolymer layer having a plurality of pores and an elastomer present in substantially all of the pores of the more than one fluoropolymer layer. Each leaflet 140 is movable between a closed position, shown in FIG. 3B, in which blood is substantially prevented from flowing through the valve assembly, and an open position, shown in FIG. 3A, in which blood is allowed to flow through the valve assembly. Thus, the leaflets 140 of the prosthetic heart valve 100 cycle between the closed and open positions generally to regulate blood flow direction in a human patient.

The performance of the prosthetic heart valve leaflets was characterized on a real-time pulse duplicator that measured typical anatomical pressures and flows across the prosthetic heart valve. The flow performance was characterized by the following process:

The valve assembly was potted into a silicone annular ring (support structure) to allow the valve assembly to be subsequently evaluated in a real-time pulse duplicator. The potting process was performed according to the recommendations of the pulse duplicator manufacturer (Vi Vitro Laboratories Inc., Victoria BC, Canada).

The potted valve assembly was then placed into a real-time left heart flow pulse duplicator system. The flow pulse duplicator system included the following components supplied by VSI Vivitro Systems Inc., Victoria BC, Canada: a Super Pump, Servo Power Amplifier Part Number SPA 3891; a Super Pump Head, Part Number SPH 5891B, 38.320 cm² cylinder area; a valve station/fixture; a Wave Form Generator, TriPack Part Number TP 2001; a Sensor Interface, Part Number VB 2004; a Sensor Amplifier Component, Part Number AM 9991; and a Square Wave Electro Magnetic Flow Meter, Carolina Medical Electronics Inc., East Bend, N.C., USA.

In general, the flow pulse duplicator system uses a fixed displacement, piston pump to produce a desired fluid flow through the prosthetic heart valve under test.

The heart flow pulse duplicator system was adjusted to produce the desired flow (5 L/min), mean pressure (15 mmHg), and simulated pulse rate (70 bpm). The prosthetic heart valve under test was then cycled for about 5 to 20 minutes.

Pressure and flow data were measured and collected during the test period, including right ventricular pressures, pulmonary pressures, flow rates, and pump piston position.

Parameters used to characterize a prosthetic heart valve are effective orifice area and regurgitant fraction. The effective orifice area (EOA), which can be calculated as follows: $EOA(cm^2) = Q_{rms}/(51.6*(\Delta P)^{1/2})$ where $Q_{rms}$ is the root mean square systolic/diastolic flow rate (cm³/s) and $\Delta P$ is the mean systolic/diastolic pressure drop (mmHg).

Another measure of the hydrodynamic performance of a prosthetic heart valve is the regurgitant fraction, which is the amount of fluid or blood regurgitated through the prosthetic heart valve divided by the stroke volume.

The hydrodynamic performance measured values were; EOA=2.06 cm², and regurgitant fraction=8.2%.

Example 2

Another prosthetic heart valve was made as described in Example 1 with the following exceptions.

Initial Assembly and Thermal Process Cycle

The diameter of the leaflet frame and outer frame were expanded slightly and received on the wrapped mandrel with 16 mm space between them, rotational alignment of the leaflet frame and outer frame was made.

Final Assembly and Thermal Process Cycle

A scalpel was used to cut above the mechanical linking tab. The tab was deformed to link the leaflet frame to the outer frame.

The resulting prosthetic heart valve 100 includes leaflets 140 formed from a composite material with more than one fluoropolymer layer having a plurality of pores and an elastomer present in substantially all of the pores of the more than one fluoropolymer layer. Each leaflet 140 is movable between a closed position, shown in FIG. 3B, in which blood is substantially prevented from flowing through the valve assembly, and an open position, shown in FIG. 3A, in which blood is allowed to flow through the valve assembly. Thus, the leaflets 140 of the prosthetic heart valve 100 cycle between the closed and open positions generally to regulate blood flow direction in a human patient.

The hydrodynamic performance was measured. The performance values were; EOA=2.3 cm² and regurgitant fraction=11.8%.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

Example 3 (Single Leaflet Frame Prosthetic Heart Valve)

In exemplary embodiments, a prosthetic heart valve having polymeric leaflets formed from a composite material having an expanded fluoropolymer membrane and an elastomeric material and joined to a semi-rigid, non-collapsible metallic frame, and further a having strain relief was constructed according to the following process:

A leaflet frame was laser machined from a length of MP35N cobalt chromium tube hard tempered with an outside diameter of 26.0 mm and a wall thickness of 0.6 mm in the shape. The leaflet frame was electro-polished resulting in 0.0127 mm material removal from each surface and leaving the edges rounded. The leaflet frame was exposed to a surface roughening step to improve adherence of leaflets to the leaflet frame. The leaflet frame was cleaned by submersion in an ultrasonic bath of acetone for approximately five minutes. The entire metal leaflet frame surface was then subjected to a plasma treatment using equipment (e.g. PVA TePLa America, Inc Plasma Pen, Corona, Calif.) and methods commonly known to those having ordinary skill in the art. This treatment also served to improve the wetting of the fluorinated ethylene propylene (FEP) adhesive.

FEP powder (Daikin America, Orangeburg N.Y.) was then applied to the leaflet frame. More specifically, the FEP powder was stirred to form an airborne "cloud" in an enclosed blending apparatus, such as a standard kitchen type blender, while the leaflet frame is suspended in the cloud. The leaflet frame was exposed to the FEP powder cloud until a layer of powder was adhered to the entire surface of the leaflet frame. The leaflet frame was then subjected to a thermal treatment by placing it in a forced air oven set to 320° C. for approximately three minutes. This caused the powder to melt and adhere as a thin coating over the entire leaflet frame. The leaflet frame was removed from the oven and left to cool to approximately room temperature.

The strain relief was attached to the leaflet frame in the following manner. A thin (122 μm) walled sintered 15 mm diameter ePTFE tube was disposed on a 24.5 mm vented metal mandrel by stretching radially over a tapered mandrel. Two layers of a substantially nonporous ePTFE membrane with a continuous FEP coating was circumferentially wrapped on the mandrel with the FEP side towards the mandrel. The wrapped mandrel was placed in a convection oven set to 320° C. and heated for 20 min. The ePTFE and substantially nonporous ePTFE membrane combined to serve as an inner release liner and was perforated using a scalpel blade to communicate pressure between the vent holes in the mandrel. This entire release liner is removed in a later step.

A 5 cm length of the thick (990μ) walled partially sintered 22 mm inner diameter ePTFE tube (density=0.3 g/cm³) was disposed onto the 24.5 mm vented metal mandrel with release liner. The ePTFE tube inner diameter was enlarged by stretching it on a tapered mandrel to accommodate the larger mandrel diameter.

A thin (4 μm) film of type 1 FEP (ASTM 03368) was constructed using melt extrusion and stretching. One layer of the FEP was wrapped over the 5 cm length of the ePTFE tube.

The FEP powder coated leaflet frame was disposed onto the vented metal mandrel generally in the middle of the 5 cm span of ePTFE tube and FEP film.

One layer of the FEP was wrapped over the leaflet frame and 5 cm length of the ePTFE tube.

A second 5 cm length of the 990 μm thick/22 mm inner diameter ePTFE tube was disposed onto the assembly layered onto 24.5 mm vented metal mandrel by stretching its radius over a tapered mandrel to accommodate the larger construct diameter.

A substantially nonporous ePTFE membrane was configured into a cylinder at a diameter larger than the construct and placed over the assembly, referred to as sacrificial tube. Sintered ePTFE fiber (e.g. Gore Rastex® Sewing Thread, Part #S024T2, Newark Del.) was used to seal both ends of the sacrificial tube against the mandrel.

The assembly, including the mandrel, was heated in a convection oven (temperature set point of 390° C.) capable of applying pneumatic pressure of 100 psi external to the sacrificial tube described above while maintaining a vacuum internal to the mandrel. The assembly was cooked for 40 min such that the mandrel temperature reached approximately 360° C. (as measured by a thermocouple direct contact with the inner diameter of the mandrel). The assembly was removed from the oven and allowed to cool to approximately room temperature while still under 100 psi pressure and vacuum.

The sacrificial tube was then removed. Approximately 30 psi of pressure was applied to the internal diameter of the mandrel to assist in removal of the assembly. The inner release liner was peeled away from the internal diameter of the assembly by inverting the liner and axially pulling it apart.

The polymeric material was trimmed with a scalpel and removed from the leaflet windows and bottom of the leaflet frame leaving approximately 0.5 to 1.0 mm of material overhang.

A leaflet material was then prepared. A membrane of ePTFE was manufactured according to the general teachings described in U.S. Pat. No. 7,306,729. The ePTFE membrane had a mass per area of 0.452 g/m², a thickness of about 508 nm, a matrix tensile strength of 705 MPa in the longitudinal direction and 385 MPa in the transverse direction. This membrane was imbibed with a fluoroelastomer. The copolymer consists essentially of between about 65 and 70 weight percent perfluoromethyl vinyl ether and complementally about 35 and 30 weight percent tetrafluoroethylene.

The fluoroelastomer was dissolved in Novec HFE7500 (3M, St Paul, Minn.) in a 2.5% concentration. The solution was coated using a mayer bar onto the ePTFE membrane (while being supported by a polypropylene release film) and dried in a convection oven set to 145° C. for 30 seconds. After 2 coating steps, the final ePTFE/fluoroelastomer or composite had a mass per area of 1.75 g/m², 29.3% fluoropolymer by weight, a dome burst strength of about 8.6 KPa, and thickness of 0.81 μm.

The final leaflet was comprised of 28.22% fluoropolymer by weight with a thickness of 50.3 μm. Each leaflet had 26 layers of the composite and a ratio of thickness/number of layers of 1.93 μm.

Figure 11C:
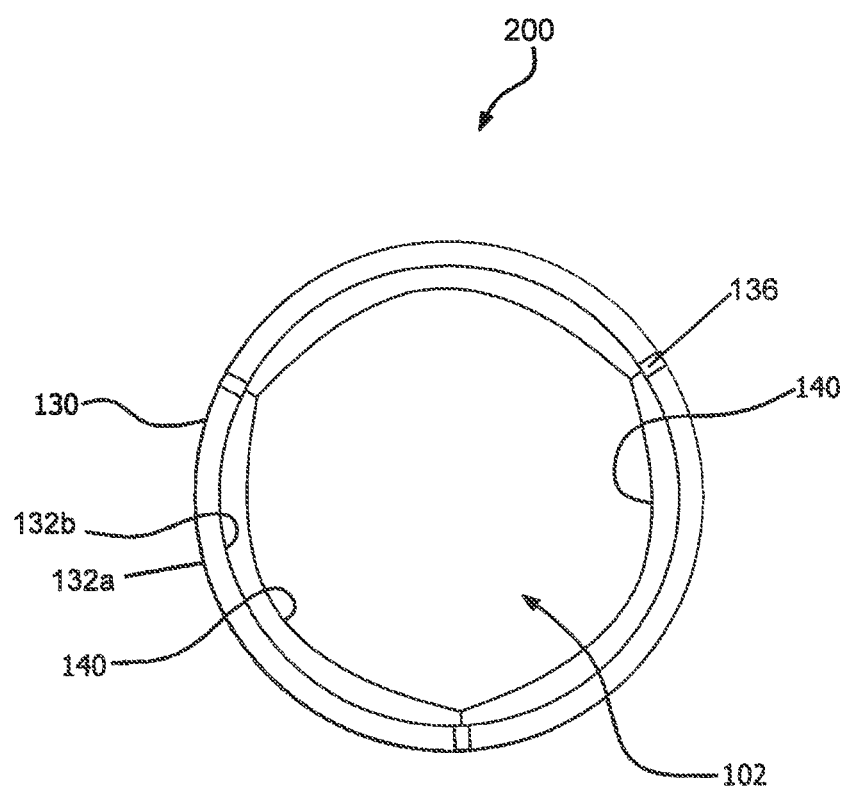
FIG. 11C is an axial or top view of the embodiment of the prosthetic heart valve of FIG. 11A in an open configuration.
Figure 11D:
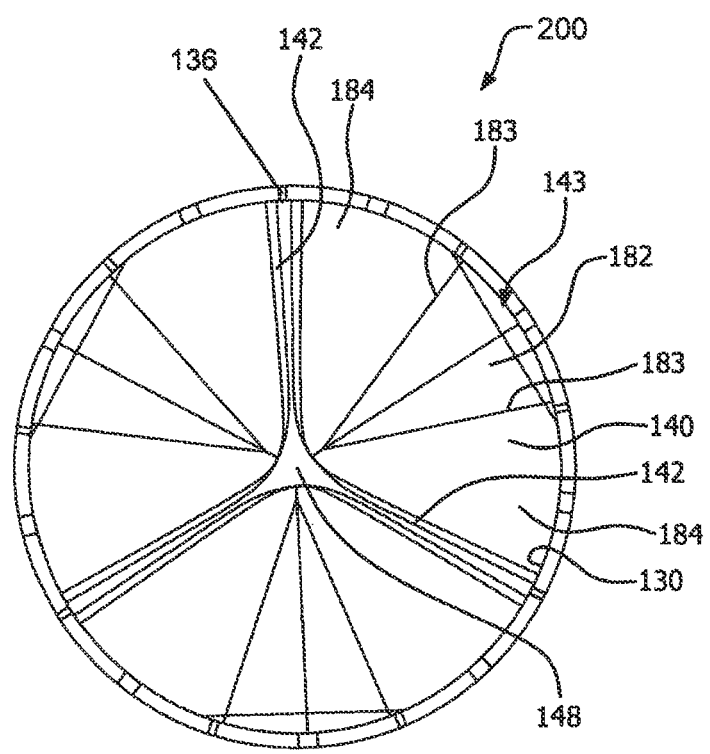
FIG. 11D is an axial or top view of the embodiment of the prosthetic heart valve of FIG. 1A in a closed configuration.

The resulting prosthetic heart valve 200 includes leaflets 140 formed from a composite material with more than one fluoropolymer layer having a plurality of pores and an elastomer present in substantially all of the pores of the more than one fluoropolymer layer. Each leaflet 140 is movable between a closed position, shown illustratively in FIG. 11D, in which blood is substantially prevented from flowing through the valve assembly, and an open position, shown illustratively in FIG. 11C, in which blood is allowed to flow through the prosthetic heart valve 200. Thus, the leaflets 140 of the prosthetic heart valve 200 cycle between the closed and open positions generally to regulate blood flow direction in a human patient.

The hydrodynamic performance was measured prior to accelerated wear testing. The performance values were; EOA=2.4 cm² and regurgitant fraction=11.94%.

It will be apparent to those skilled in the art that various modifications and variations can be made in the present embodiments without departing from the spirit or scope of the embodiments. Thus, it is intended that the present embodiments cover the modifications and variations of this invention provided they come within the scope of the appended claims and their equivalents.

What is claimed:

1. A prosthetic valve, comprising:
a leaflet frame having a tubular shape, the leaflet frame defining a plurality of leaflet windows wherein each of the leaflet windows includes two leaflet window sides, a leaflet window base, and a leaflet window top; and
a film coupled to the leaflet frame and defining a plurality of leaflets, one of the plurality of leaflets being coupled to and extending from each of the leaflet windows, wherein each leaflet has the shape of an isosceles trapezoid having two leaflet sides, a leaflet base and a leaflet free edge opposite the leaflet base, wherein the two leaflet sides diverge from the leaflet base, wherein the leaflet base is substantially flat, wherein the leaflet base of each leaflet is truncated in which the leaflet in cross section shows a line in an alpha plane onto the leaflet frame, in which the truncation is a straight line across the leaflet base of the leaflet and perpendicular to a valve axis, wherein the leaflet base is coupled to the leaflet window base and wherein each of the two leaflet sides are coupled to one of the two leaflet window sides.

2. The prosthetic valve of claim 1, wherein each leaflet includes a central region and two side regions on opposite sides of the central region, wherein the central region is defined by a shape of an isosceles triangle defined by two central region sides, the leaflet base and the leaflet free edge, wherein the two central region sides converge from the leaflet base, and wherein each of the side regions have a shape of a triangle and each are defined by one of the central region sides, one of the leaflet sides, and the leaflet free edge.

3. A prosthetic valve, comprising:
a leaflet frame; and
a plurality of leaflets coupled to the leaflet frame, each leaflet including a free edge and a base, wherein the base of each leaflet is truncated in which a cross section of the leaflet that is parallel with a valve axis at the base defines a straight line in an alpha plane, in which the truncation defines a straight line across the base of the leaflet that is perpendicular to the valve axis, wherein the alpha plane is perpendicular to the valve axis and passes through the base.

4. The prosthetic valve of claim 3, further comprising:
an outer frame having a tubular shape, the leaflet frame having a tubular shape and defining a plurality of leaflet windows, the leaflet frame and outer frame coupled at least in part by a contiguous portion of a film, at least a first portion of the contiguous portion of the film being contained between and coupling the leaflet frame and outer frame that minimizes relative movement and prevents contact between the leaflet frame and outer frame, wherein a second portion of the contiguous portion of the film defines each leaflet that extends from each of the leaflet windows.

5. The prosthetic valve of claim 3, in which truncation of each leaflet is located inferior and exterior to a line joining apices of two adjacent commissural posts.

6. The prosthetic valve of claim 3, the leaflet frame having a tubular shape, the leaflet frame defining a plurality of leaflet windows wherein each of the leaflet windows includes two leaflet window sides, a leaflet window base, and a leaflet window top; and
a film coupled to the leaflet frame and defining at least one leaflet extending from each of the leaflet windows, wherein each leaflet has the shape of an isosceles trapezoid having two leaflet window sides, a leaflet base and a free edge opposite the leaflet base, wherein the two leaflet sides diverge from the leaflet base, wherein the leaflet base is substantially flat, wherein the leaflet base is coupled to the window base and wherein each of the two leaflet sides are coupled to one of the two window sides.

7. The prosthetic valve of claim 6, wherein each leaflet includes a central region and two side regions on opposite sides of the central region, wherein the central region is defined by a shape of an isosceles triangle defined by two central region sides, the leaflet base and the leaflet free edge, wherein the two central region sides converge from the leaflet base, and wherein each of the side regions have a shape of a triangle and each are defined by one of the central region sides, one of the leaflet sides, and the leaflet free edge.

* * * * *